(12) United States Patent
Shaanan et al.

(10) Patent No.: US 9,308,324 B2
(45) Date of Patent: Apr. 12, 2016

(54) PORTABLE MEDICINE INJECTION DEVICE AND ANALYTE METERING SYSTEM

(71) Applicant: YofiMeter, LLC, La Jolla, CA (US)

(72) Inventors: Gad Shaanan, La Jolla, CA (US); Marc Goldman, La Jolla, CA (US)

(73) Assignee: YOFIMETER, LLC, La Jolla, CA (US)

( * ) Notice: Subject to any disclaimer, the term of this patent is extended or adjusted under 35 U.S.C. 154(b) by 0 days.

(21) Appl. No.: 14/371,401

(22) PCT Filed: Sep. 26, 2013

(86) PCT No.: PCT/US2013/062048
§ 371 (c)(1),
(2) Date: Jul. 9, 2014

(87) PCT Pub. No.: WO2014/052676
PCT Pub. Date: Apr. 3, 2014

(65) Prior Publication Data
US 2015/0190577 A1 Jul. 9, 2015

Related U.S. Application Data

(60) Provisional application No. 61/706,071, filed on Sep. 26, 2012.

(30) Foreign Application Priority Data

Mar. 6, 2013 (CA) ..................................... 2808738

(51) Int. Cl.
| | | |
|---|---|---|
| *A61M 5/20* | (2006.01) | |
| *A61M 5/28* | (2006.01) | |
| *A61M 5/315* | (2006.01) | |
| *G06F 19/00* | (2011.01) | |
| *A61M 5/142* | (2006.01) | |
| *A61M 5/145* | (2006.01) | |
| *A61M 5/24* | (2006.01) | |

(52) U.S. Cl.
CPC . *A61M 5/20* (2013.01); *A61M 5/28* (2013.01); *A61M 5/3158* (2013.01);
(Continued)

(58) Field of Classification Search
CPC ... A61M 5/24; A61M 5/1452; A61M 5/1454; A61M 5/31551; A61M 5/31561; A61M 5/3158; A61M 5/31543; A61M 5/31558; A61M 5/31575; A61M 5/31528; A61M 2005/31518; A61M 5/20; A61M 5/28; A61M 5/31585; A61M 5/581; A61M 5/14244; A61M 2005/2407; A61M 2005/145; A61M 2230/201; A61M 2205/50; A61M 2205/581; A61M 2205/3592; G06F 19/3468
See application file for complete search history.

(56) References Cited

U.S. PATENT DOCUMENTS

| | | | | |
|---|---|---|---|---|
| 5,261,882 A | * | 11/1993 | Sealfon | ............... A61M 5/1454 128/DIG. 12 |
| 6,110,149 A | * | 8/2000 | Klitgaard | ............... A61M 5/24 604/207 |

(Continued)

FOREIGN PATENT DOCUMENTS

WO    2008122139 A1    10/2008

OTHER PUBLICATIONS

Han, Inho, International Search Report and Written Opinion, PCT Application No. PCT/US2013/062048, dated Dec. 18, 2013, 13 pages.

*Primary Examiner* — Bhisma Mehta
*Assistant Examiner* — Jenna Zhang
(74) *Attorney, Agent, or Firm* — Knobbe Martens Olson & Bear LLP

(57) ABSTRACT

Methods, systems, and devices are described for setting a dose of medicine and injecting the medicine. In one aspect, a method to dispense a medicine includes inserting a cartridge containing a medicine into a cartridge holder coupled to a housing of a medicine injection device, positioning a spine component of the device to make contact with the cartridge in the cartridge holder, selecting a dose of the medicine for injection, in which the selecting includes rotating an injection component of the device to a setting corresponding to the selected dose, and linearly advancing the injection component to rotate a drive gear coupled to the injection component to drive the spine component so as to push the end of the cartridge to dispense the medicine in the amount of the selected dose.

19 Claims, 18 Drawing Sheets

(52) U.S. Cl.
CPC ...... *A61M 5/31551* (2013.01); *A61M 5/31561* (2013.01); *A61M 5/31575* (2013.01); *A61M 5/31585* (2013.01); *G06F 19/3468* (2013.01); *A61M 5/1454* (2013.01); *A61M 5/14244* (2013.01); *A61M 5/24* (2013.01); *A61M 5/31528* (2013.01); *A61M 5/31543* (2013.01); *A61M 5/31558* (2013.01); *A61M 2005/14506* (2013.01); *A61M 2005/2407* (2013.01); *A61M 2005/31518* (2013.01); *A61M 2205/3584* (2013.01); *A61M 2205/3592* (2013.01); *A61M 2205/50* (2013.01); *A61M 2205/581* (2013.01); *A61M 2230/201* (2013.01)

(56) References Cited

U.S. PATENT DOCUMENTS

| | | | |
|---|---|---|---|
| 7,713,238 B2* | 5/2010 | Mernoe | A61M 5/14244 604/131 |
| 7,794,427 B2* | 9/2010 | Estes | A61M 5/14244 417/411 |
| 8,105,279 B2* | 1/2012 | Mernoe | A61M 5/14244 417/46 |
| 2002/0151855 A1* | 10/2002 | Douglas | A61M 5/31511 604/218 |
| 2004/0087904 A1* | 5/2004 | Langley | A61M 5/20 604/131 |
| 2004/0122368 A1* | 6/2004 | Langley | A61M 5/31513 604/151 |
| 2007/0066938 A1* | 3/2007 | Iio | A61B 5/1411 604/152 |
| 2007/0093761 A1* | 4/2007 | Veasey | A61M 5/31546 604/207 |
| 2007/0197968 A1* | 8/2007 | Pongpairochana | A61M 5/20 604/131 |
| 2010/0256565 A1 | 10/2010 | Mernoe et al. | |
| 2011/0245773 A1 | 10/2011 | Estes et al. | |

* cited by examiner

PORTABLE MEDICINE INJECTION DEVICE AND ANALYTE METERING SYSTEM

CROSS REFERENCE TO RELATED APPLICATIONS

This patent document is a 35 U.S.C. §371 National Stage application of International Application No. PCT/US2013/062048 filed Sep. 26, 2013, which claims the benefit of priority from Canadian Patent Application No. 2,808,738, entitled "PORTABLE MEDICINE INJECTION DEVICE AND ANALYTE METERING SYSTEM" filed Mar. 6, 2013, now granted as Canadian Patent No. 2,808,738, on Mar. 18, 2014. This document further claims the benefit of priority from U.S. Provisional Application No. 61/706,071 entitled "PORTABLE MEDICINE INJECTION DEVICE" filed on Sep. 26, 2012. The entire disclosure of the above-referenced applications is incorporated by reference as part of the specification of this application.

TECHNICAL FIELD

This patent document relates to medicine injection devices technologies, including portable medicine injection devices such as portable insulin injection devices for self-administration by diabetic patients.

BACKGROUND

Diabetes mellitus is a group of metabolic diseases associated with high blood sugar, e.g., which may be due to insufficient production of insulin by the body or inadequate response by cells to the insulin that is produced. There are three main types of diabetes mellitus (diabetes). Type 1 diabetes results from the body's failure to produce insulin, and presently requires the person to inject insulin (e.g., manually or using a wearable insulin pump). Type 2 diabetes results from insulin resistance, in which cells fail to use insulin properly, sometimes combined with an absolute insulin deficiency. Types 1 and 2 diabetes are considered chronic conditions that cannot be cured. The third main form, referred to as gestational diabetes, can occur when pregnant women without a previous history of diabetes develop a high blood glucose level, e.g., which can develop into type 2 diabetes, but often resolves after the pregnancy. Other forms of diabetes include congenital diabetes (e.g., due to genetic defects of insulin secretion), cystic fibrosis-related diabetes, steroid diabetes (e.g., due to high doses of glucocorticoids), and other forms of monogenic diabetes.

For example, diabetes, without proper treatment, may cause acute complications, e.g., including hypoglycemia, diabetic ketoacidosis, or nonketotic hyperosmolar coma, or in some instances, may cause serious long-term complications, e.g., cardiovascular disease, chronic renal failure, and/or diabetic retinopathy (retinal damage). Adequate treatment of diabetes is thus important, as well as controlling blood pressure and managing lifestyle factors such as nonsmoking and healthy body weight. Insulin is used to treat the many of the forms of diabetes, including type 1 diabetes. Other medications are used to treat type 2 diabetes.

SUMMARY

Systems, devices, and techniques are described for injecting a medicine using a mechanical dose setting and dispensing mechanism with built in intelligence to track the use of the medicine and communicate the data in a closed loop system.

In one aspect of the disclosed technology, a method to dispense a medicine includes inserting a cartridge containing a medicine into a cartridge holder coupled to a housing of a medicine injection device, positioning a spine component of the device to make contact with the cartridge in the cartridge holder, selecting a dose of the medicine for injection, in which the selecting includes rotating an injection component of the device to a setting corresponding to the selected dose, and linearly advancing the injection component to rotate a drive gear coupled to the injection component to drive the spine component so as to push the end of the cartridge to dispense the medicine in the amount of the selected dose.

In another aspect, a device to dispense a medicine includes a housing configured to include a curved channel, a cartridge holder coupled to the housing via a pivot joint, the cartridge holder including a chamber structured to encase a cartridge containing a medicine and having a first opening that aligns with one end of the curved channel and a second opening at the opposite end of the chamber, and a dose setting and injecting mechanism. The dose setting and injection mechanism includes (i) a spine component housed in the curved channel of the housing, the spine component including a plurality of link structures linked together to allow curved movement of the spine component within the curved channel, in which the one end of the curved channel includes a channel opening interfaced with the first opening to enable the spine component to push against the cartridge for dispensing a selected amount of the medicine through the second opening, (ii) a shaft component structured to include a threaded cylindrical section encased at least in part within the housing and a knob disposed at least in part outside of the housing, (iii) a gear mechanism including a rod having a first gear and a second gear which is coupled to the spine component, and a drive gear having a first gear engagement for engaging to the first gear and a second gear engagement for engaging to threads of the threaded cylindrical section of the shaft component, in which, upon engaging the first gear and the drive gear to each other, a linear movement of the shaft component moves the spine component, and (iv) a disengagement button coupled to the rod to disengage the first gear and the drive gear from each other, e.g., to allow the spine component to move independent of the shaft component. The device can be operated such that a rotation of the shaft component moves the shaft component to a distance from the housing that corresponds selected amount of the medicine.

In another aspect, a health management system includes an analyte monitoring device to determine a concentration level of an analyte; a computing system in communication with the analyte monitoring device, in which the computing system includes a memory unit and a processor configured to process data; and a medicine injection device in communication with at least one of the analyte monitoring device or the computing system. The medicine injection device includes a housing configured to include a curved channel, a cartridge holder coupled to the housing via a pivot joint, the cartridge holder including a chamber structured to encase a cartridge containing a medicine and having a first opening that aligns with a first end of the curved channel and a second opening, and a dose setting and injecting mechanism. The dose setting and injection mechanism includes (i) a spine component housed in the curved channel of the housing, the spine component including a plurality of link structures linked together to allow curved movement of the spine component within the curved channel, in which the first end of the curved channel includes a channel opening interfaced with the first opening to enable the spine component to push against the cartridge for dispensing a selected amount of the medicine through the second opening, (ii) a shaft component structured to include a threaded cylindrical section encased at least in part within the housing and a knob disposed at least in part outside of the housing, (iii) a gear mechanism including a rod having a first gear and a second gear, the second gear coupled to the spine component, and a drive gear having a first gear engagement mechanism for engaging to the first gear and a second gear engagement mechanism for engaging to threads of the threaded cylindrical section of the shaft component, in which, upon engagement of the first gear and the drive gear to each other, a linear movement of the shaft component moves the spine component, and (iv) a disengagement button coupled to the rod to disengage the first gear and the drive gear from each other, thereby allowing the spine component to move independent of the shaft component, in which a rotation of the shaft component moves the shaft component to a distance from the housing that corresponds to the selected amount of the medicine.

The subject matter described in this patent document can be implemented in specific ways that provide one or more of the following features. For example, the disclosed medicine dispensing device can be configured to have a small, compact size enabling convenient portability of the device, e.g., in which a user can store within one's pocket, purse, handbag, etc. For example, the disclosed medicine dispensing device can include an electronic display that provides the user with information including, but not limited to, a current dose setting that the device is dialed to inject, the amount of medicine previously injected from the existing loaded medicine cartridge in the device, the type of medicine in the loaded cartridge (e.g., such as the name of the drug, manufactured lot number, etc.), when to perform medicine injections, and instructions for the user about the use of the device or status of the device. For example, the disclosed medicine dispensing device can include a cartridge holder that opens and closes in a manner that provides ease of loading and removal of a medicine cartridge. For example, the disclosed medicine dispensing device can include an optical scanner that can scan an identification code located on the medicine cartridge and detect the type of medicine contained in the cartridge, e.g., which can be processed as data in the device. For example, the disclosed medicine dispensing device can be implemented as a reusable medicine dispensing pen that communicates wirelessly with other devices, e.g., such as a blood glucose monitor, mobile phone or computing device including a user interface for health management (e.g., including glucose monitoring and insulin treatments), creating a closed loop system that provides convenience and ease of use for a user to monitor analyte levels and perform drug-related treatments. For example, the closed loop system can enable the information stored on the disclosed medicine injection device to be relayed (e.g., such as the type, amount, and injection time of a medicine) to other device(s), which can store the reported information as data and utilize the stored data with other user data that can be used in health management, e.g. in real time).

BRIEF DESCRIPTION OF THE DRAWINGS

Like reference symbols and designations in the various drawings indicate like elements.

DETAILED DESCRIPTION

Figure 1A:
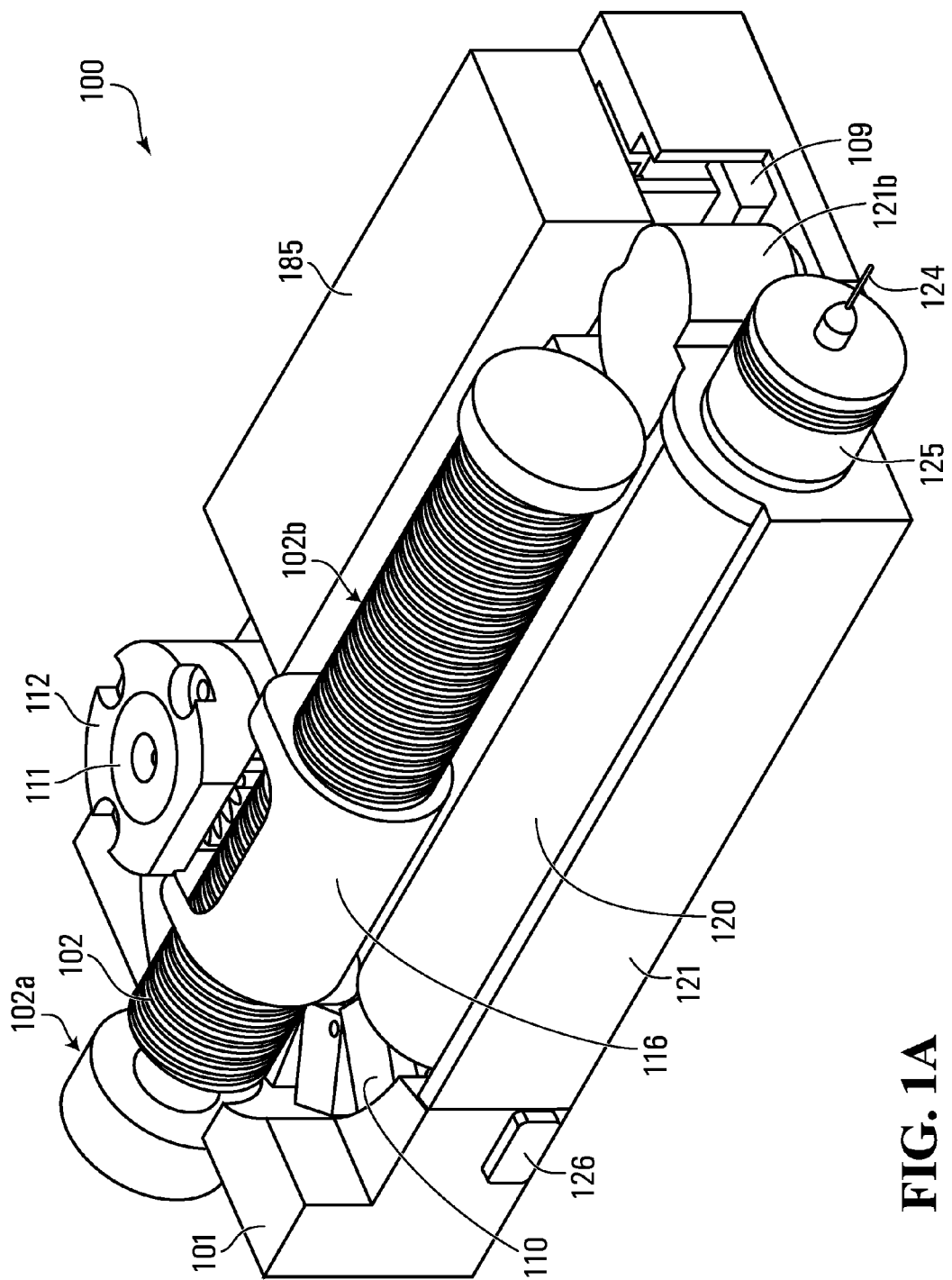
FIGS. 1A-1F show schematics of an exemplary medicine injection device based on the disclosed technology.

The technologies and technical features described in this document can be implemented to provide portable insulin injection devices for self-administration by diabetic patients. The described technologies and technical features can be implemented in various medicine injection devices including portable medicine injection devices other than the portable insulin injection devices.

A portable insulin injection device can be configured as a compact insulin pen for injecting insulin as part of treatment and/or management of diabetic conditions in a patient. For example, an insulin pen device can include an insulin cartridge holder and mechanisms to dial to measure a dose of the insulin and to dispense the measured dose. The insulin pen device can include a housing structure which can be shaped like a pen or other suitable geometries for encasing or holding the insulin contained in a cartridge, which can also be referred to as a container or vial. The insulin pen device also includes a mechanism that uses disposable needles to inject the dose into the patient's body. Insulin pens can be configured as disposable pens that do not replace vials of insulin after use or as reusable pens that allow for replaceable insulin cartridges to be loaded into the cartridge holder of the pen device. For example, insulin pens can be configured to provide advantages over vial and syringe modalities that include greater convenience in portability for daily use and transport, increased accuracy in doses, improved ease to implement (e.g., particularly among those with visual or fine motor skills impairments), and reduced pain caused by injection.

Yet, some existing modalities of insulin treatments for diabetic patients suffer certain problems and inefficiencies. For example, in some existing insulin injection devices, unless a pump is used, an insulin dose for injection needs to be tracked and recorded manually. For example, some existing insulin injection devices do not provide an insulin pen that is integrated with a blood glucose monitor device to track test results and insulin dosage. For example, various existing insulin injection devices have designs that render it difficult to accurately administer using insulin pens, e.g., various features associated with the mechanics of the pen devices to set a dose, prime the injection, and replace the insulin cartridge may cause the above mentioned difficulty. Additionally, for example, some existing insulin pen devices include large physical dimensions that are inconvenient for a user to portably carry and store. In some existing insulin injection devices, spent cartridges of reusable insulin pens are difficult to remove, making it inconvenient for the patient to reset the pen for next use. Disposable insulin injection pens may provide convenient features in some regards but they tend to be expensive on a per use basis and also do not include tracking and reporting functionalities.

Disclosed are systems, devices, and techniques for injecting a medicine including insulin using a precise mechanical dose setting and a convenient and accurate dispensing mechanism with built in intelligence to track the use of the medicine and communicate the data in a closed loop system. While the disclosed embodiments described in this patent document are primarily based on systems, devices and techniques to inject insulin, e.g., in order to facilitate understanding of the underlying concepts, it is understood that the disclosed embodiments can also be used for injection of other medicines.

In one embodiment of the disclosed technology, a device can include a mechanical dose setting and dispensing mechanism with integrated electronics to monitor and display the use of the medicine and communicate the data in a closed loop system. For example, the exemplary medicine injection device can include a housing configured to include a curved channel, a medicine cartridge holder coupled to the housing (e.g., via a pivot joint), in which the cartridge holder includes a chamber structured to encase a cartridge containing a medicine and having a first opening that aligns with one end of the curved channel and a second opening at the opposite end of the chamber, and a dose setting and injecting mechanism. The dose setting and injection mechanism can include (i) a spine component housed in the curved channel of the housing, the spine component including a plurality of link structures linked together to allow curved movement of the spine component within the curved channel, in which the one end of the curved channel includes a channel opening interfaced with the first opening to enable the spine component to push against the medicine cartridge for dispensing a selected amount of the medicine through the second opening, (ii) a shaft component structured to include a threaded cylindrical section encased at least in part within the housing and a knob disposed at least in part outside of the housing, (iii) a gear mechanism including a rod having a first gear and a second gear which is coupled to the spine component, and a drive gear having a first gear engagement for engaging to the first gear and a second gear engagement for engaging to threads of the threaded cylindrical section of the shaft component, in which, upon engaging the first gear and the drive gear to each other, a linear movement of the shaft component moves the spine component, and (iv) a disengagement button coupled to the rod to disengage the first gear and the drive gear from each other, e.g., to allow the spine component to move independent of the shaft component. The exemplary medicine injection device can be operated such that a rotation of the shaft component moves the shaft component to a distance from the housing that corresponds selected amount of the medicine.

In some examples, the drive gear of the gear mechanism can be structured to include external threads that couple to the shaft component between threads of the threaded cylindrical section and internal threads located within a hole through the center of the drive gear, in which the drive gear moves in response to a movement of the shaft component. For example, the rod can intersect through the drive gear via the hole and be structured to include a threaded gear (e.g., the first gear) and an indentation, in which the threaded gear is capable of coupling to the drive gear between internal threads when the gear mechanism is in an engaged position. The rod can also include a second gear located between the threaded gear and the indentation. For example, the second gear of the rod can be structured to include outer threads that couple between threads of the link structures of the spine component. For example, an advancement of the disengagement button advances the rod from the engaged position to a disengaged position that disengages the drive gear from the threaded gear of the rod, e.g., allowing the spine component to move independent of the shaft component.

For example, the exemplary medicine injection device can also include a data processing unit that includes a processor and a memory unit, in which the selected dose for an injection and dispensed dose are processed as data by the processor and stored in the memory unit. For example, the exemplary medicine injection device can also include a wireless transmitter unit to transmit the data to another mobile and/or computing device or system. For example, the exemplary medicine injection device can also include an electronic display that provides the user with information including, but not limited to, a current dose setting that the device is dialed to inject, the amount of medicine previously injected from the existing loaded medicine cartridge in the device, the type of medicine in the loaded cartridge (e.g., such as the name of the drug, manufactured lot number, etc.), when to perform medicine injections, and instructions for the user about the use of the device or status of the device. For example, exemplary medicine injection device can also include an optical scanner located within the housing and coupled to the data processing unit, in which the optical scanner includes an optical sensor (e.g., a laser scanner) that can scan an identification code located on a cartridge of medicine and detect the type of medicine contained in the cartridge, e.g., which can be processed as data in the device. For example, the identification code can be configured to include bars (e.g., of varying thicknesses, spacing, opacity, color, or other parameters) that radially wrap around the cylindrical casing of the medicine cartridge. In this exemplary configuration, the optical scanner can detect the identification code in any orientation that the cartridge is placed within the cartridge holder, e.g., such that the cartridge position (rotationally) is not critical to the ability to detect the identification code.

The disclosed medicine injection device can be configured to have a small, compact size enabling convenient portability of the device, e.g., in which a user can store within one's pocket, purse, handbag, etc. For example, the cartridge holder of the disclosed device can be configured to open and close in a manner that provides ease of loading and removal of a medicine cartridge. For example, the disclosed device can be implemented as a reusable medicine dispensing pen that communicates wirelessly with other devices, e.g., such as a blood glucose monitor or mobile phone or computing device including a user interface for health management (e.g., including glucose monitoring and insulin treatments), creating a closed loop system that provides convenience and ease of use for a user to monitor analyte levels and perform drug-related treatments. For example, the closed loop system can enable the information stored on the disclosed medicine injection device to be relayed (e.g., such as the type, amount, and injection time of a medicine) to other device(s), which can store the reported information as data and utilize the stored data with other user data that can be used in health management, e.g. in real time).

Figure 1B:
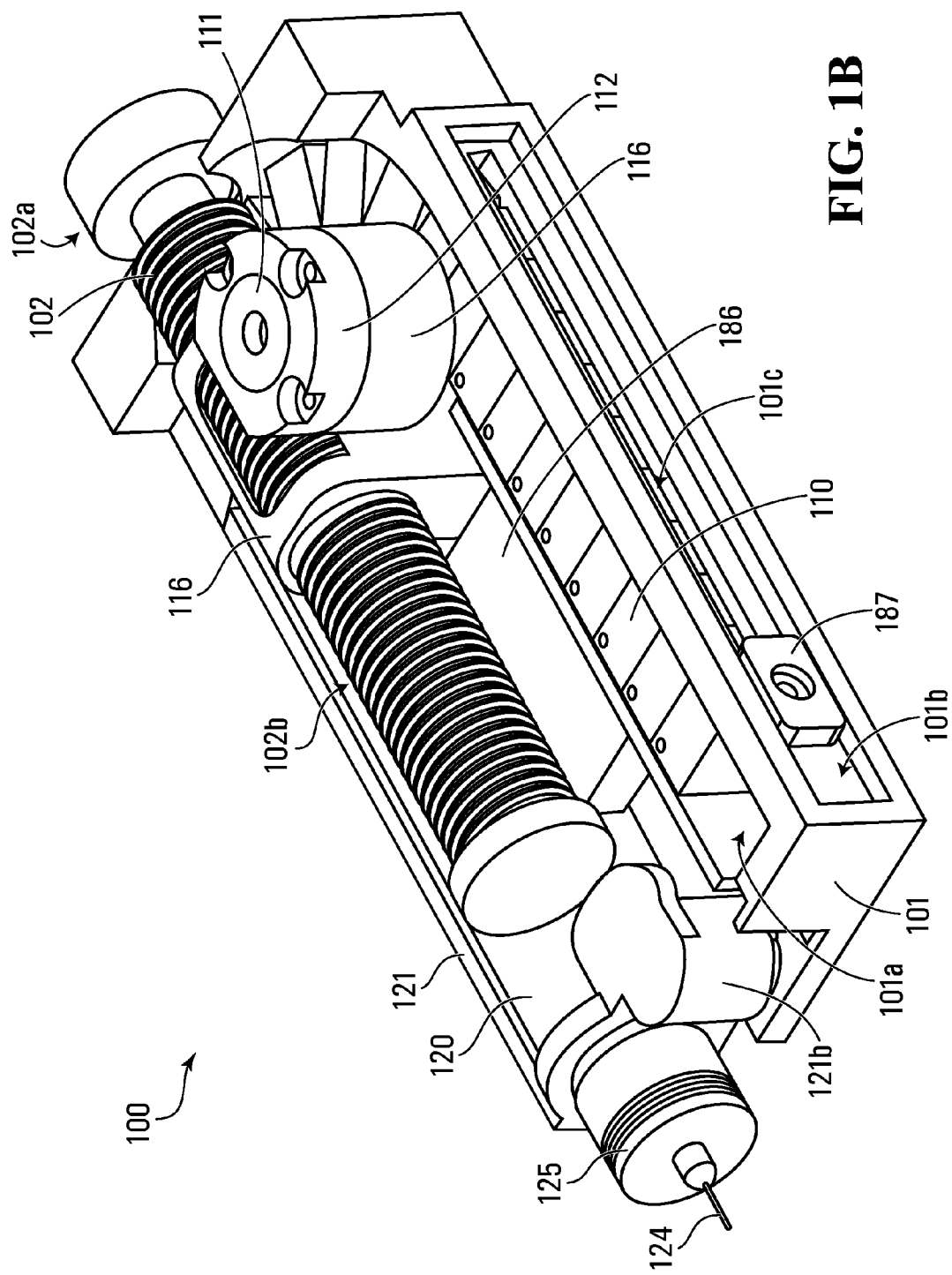

FIGS. 1A-1F show schematics of an exemplary medicine injection device 100 based on the disclosed technology. FIGS. 1A and 1B show different three dimensional cross sectional views of the components that make up the dose setting and injecting mechanism in the medicine injection device 100. It is noted that some components included in the medicine injection device 100 may not necessarily be shown in the schematics of FIGS. 1A and 1B.

As shown in FIGS. 1A and 1B, the dose setting and injecting mechanism is encased in a housing structure 101 that can be used to provide positioning and/or structural support to various mechanisms, modules and components contained with the housing of the medicine injection device 100. The device 100 includes a cartridge holder 121 that is coupled to the housing structure 101 and includes a chamber structured to encase and hold a cartridge 120 containing a medicine, e.g., insulin. The cartridge holder 121 has one end that is engaged to a rotational pivot joint structure 121b to enable the cartridge holder 121 to be in a latched position in the housing structure 101 or in an open position that exposes the chamber after being released from the latched position in the housing structure 101 for removing or replacing the cartridge 120. The rotational pivot joint structure 121b can include a spring mechanism having a torsional spring that pushes the cartridge holder 121 to an open position, as shown later in FIGS. 3A-3C. The cartridge 120 can be loaded into the chamber of the cartridge holder 121 and can be removed and replaced after the medicine in the cartridge 120 is used up or otherwise needs to be disposed or replaced. The exterior of the cartridge holder 121 at the distal end adjacent to the rotational pivot joint structure 121b includes an opening between the chamber and an attachment structure (e.g., such as a protruding or receding threading for screwing a needle on) to attach a detachable needle structure 125 with a protruding needle 124, e.g., for injecting the medicine into the patient. For example, the detachable needle structure 125 includes a cap region that attaches to the attachment structure of the cartridge holder 121. For example, the protruding needle 124 can be configured as a single needle that protrudes internally within the cap of the detachable needle structure 125 and externally from the exterior of the detachable needle structure 125.

For example, the cartridge 120 can be structured as a hollowed tube (e.g., of a non-fouling, biocompatible material) with one end configured as a medicine dispensing tip having a dispensing aperture, e.g., in which the tip region of the cartridge 120 tapers from the body of the tube structure, e.g., such that the diameter of the aperture is smaller than that of the tube body. The dispensing aperture can be covered with a membrane that seals the aperture to prevent leakage or contamination of the stored medicine in the cartridge 120. The other end of the tube structure of the cartridge 120 can be configured to include a moveable piston or plunger (e.g., of a rubber or plastic material, which can be of coated by a non-fouling, biocompatible material) initially positioned at the end within the hollowed tube. For example, the piston or plunger can function as a pliable stopper that can be pushed into the tube interior in the direction of the dispensing aperture, e.g., to push the medicine through the dispensing aperture and the protruding needle 124. For example, when the cartridge 120 is loaded into the chamber of the cartridge holder 121, the inner protruding region of the protruding needle 124 of the detachable needle structure 125 punctures through the membrane at the dispensing aperture, e.g., thereby allowing the medicine to flow through the protruding needle 124 to be dispensed from the device 100. The device 100 includes a latch mechanism 126 that can include a sliding button configured on the exterior of the housing structure 101 to move in a linear direction to unlock the latch mechanism 126 from the cartridge holder 121 to allow the cartridge holder 121 to move to the open position. The device 100 includes an electronics unit 185 including display electronic components (e.g., liquid crystal display (LCD) electronics) that can display information related to the medicine, medicine injection dose, and the device.

The device 100 can include a data processing unit 186 including a processor and a memory coupled to the processor. The data processing unit 186 in this example is shown to be a separate unit from the electronics unit 185 and is positioned underneath of the electronics unit 185. In other implementations, the electronics unit 185 and data processing unit 186 may be integrated into one module as a single unit. The data processing unit 186 can be configured to continuously monitor data provided by sensors configured along a travel path of a push spine component 110 of the dose setting and injecting mechanism to determine the movement of the push spine component 110 and process the data as an administered or dispensed dose of the medicine. For example, the processing unit 186 can report the dispensed dose data and/or provide alarms regarding the dose to a user on a display (e.g., via the display electronics of the electronics unit 185) on the exterior of the device 100, e.g., which can confirm to the user that a complete injection dose was administered. The data processing unit 186 can be configured to continuously monitor data provided by sensors configured along a travel path of an injection shaft component 102 of the dose setting and injecting mechanism to determine the movement of the injection shaft component 102 and process the data as a selected or set dose of the medicine to be dispensed. The sensors configured within the travel path of the injection shaft component 102 can measure the rotation and/or related (linear) translation of the injection shaft component 102 to indicate the selected dose. Exemplary sensors can include a linear encoder that can be optical, magnetic, or capacitive to perform the dose volume metering. For example, the processing unit 186 can report the selected dose data and/or provide alarms regarding the dose to a user on the display of the device 100, which can confirm to the user that the desired dose was dialed. For example, the data processing unit 186 can be in wired or wireless communication with a mobile device (e.g., such as a cell phone) or a computing device that includes a application portal featuring a user interface that the user of the device 100 can use for various functions, including, but not limited to, monitoring the status of the device 100 (e.g., such as if the device is ready to dispense the medicine, a setting value of the medicine to be dispensed, etc.), the presence of a cartridge in the cartridge holder 121, or the amount of medicine contained in the cartridge 120. Some examples for wireless communications of the device 100 include 3G wireless communication standards, 4G wireless communication standards including, LTE, WiFi, Bluetooth, Bluetooth LE, and other suitable wireless communications via radio frequency waves and other electromagnetic waves.

The dose setting and injecting mechanism can include a push spine component 110 encased in a curved channel 101a of the housing structure 101, an injection shaft component 102 having a threaded cylindrical section 102b at least partially encased within the housing structure 101 and a knob section 102a disposed at least partially outside of the housing structure 101, and a button 111 partially encased within a button casing structure 112 structured to expose a top surface of the button 111 outside of the housing structure 101. The dose setting and injecting mechanism can also include a gear mechanism to interact with the push spine component 110, the injection shaft component 102, and the button 111 and can be encased within a mechanism encasement structure 116 located within the housing structure 101. The mechanism encasement structure 116 can include multiple sections having to two joined chambers, in which one chamber includes a hollowed cylindrical chamber structured to encase at least a portion of the threaded cylindrical section 102b of the shaft component 102 and in which the other chamber is structured to fit the components of the gear mechanism.

Referring to FIG. 1B, the housing structure 101 can include a recess 101b along one side of the device 100, in which an opening track 101c is structured between the straight region of the curved channel 101a and the outside of the device 100. The opening track 101c provides an aperture that enables a sliding button 187 positioned within the recess 101b and coupled to the push spine component 110 (e.g., encased in the curved channel 101a) to move along the recess 101b in response to a movement of the push spine component 110.

Figure 1C:
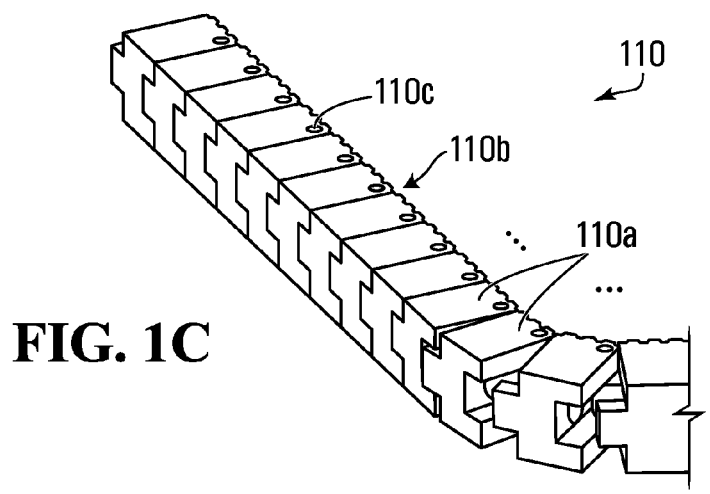

FIG. 1C shows a schematic of one example of the push spine component 110 of the dose setting and injecting mechanism. In this example, the push spine component 110 can include multiple link structures 110a formed of a rigid body that are linked together at a rotational joint 110c. The location of the rotational joint 110c on each link structure 110a can be configured near one side of the link structure 110a having threads such that the alignment of the link structures 110a positions the threads 110b on one side of the push spine component 110. For example, the rotational joint 110c can include a pin that can pass through an opening in two overlapping sections of two adjacent link structures 110a to provide a pivot in which one link structure can rotate about the other. The rotational joint 110c enables the push spine component 110 to bend in the curved section while traveling in the curved channel 101a.

Figure 1D:
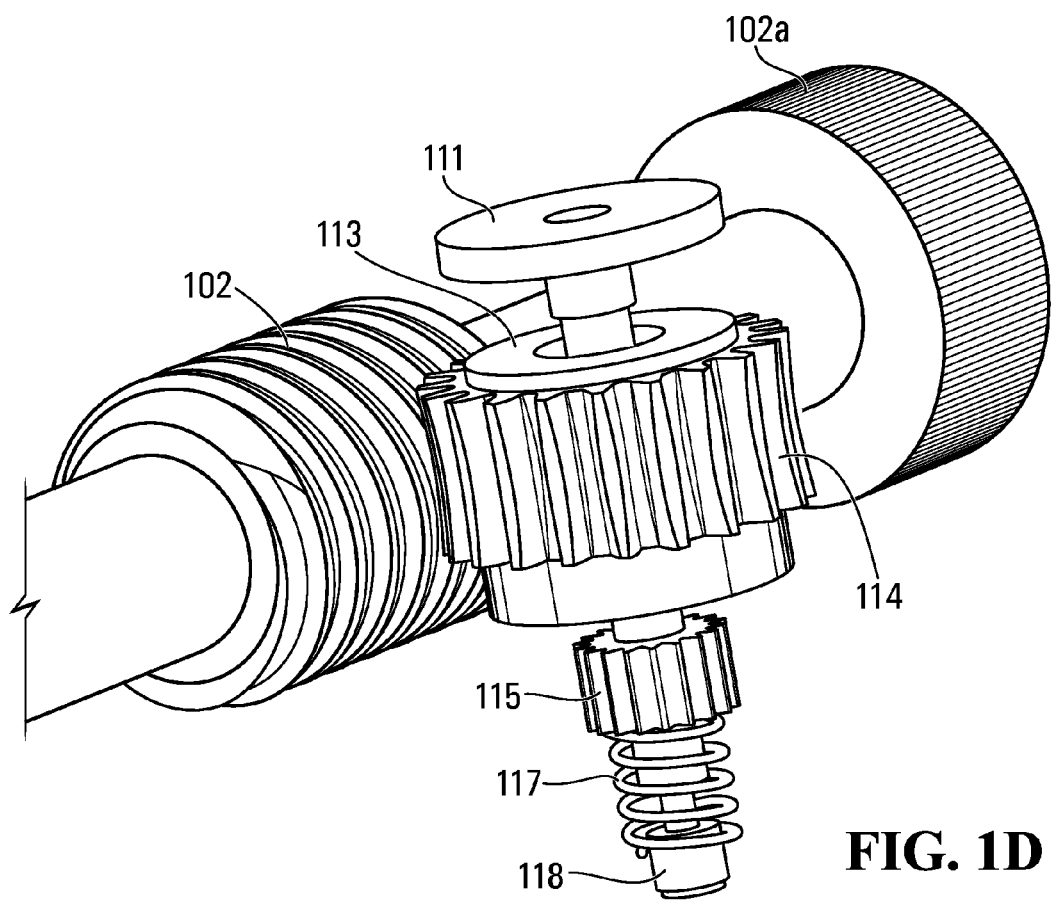

FIG. 1D shows a schematic of one example of the gear mechanism of the dose setting and injecting mechanism. In this example, the gear mechanism can include a rod shaft 118 coupled to the lower region of the button 111 at one end of the rod shaft 118 and intersecting through a roller clutch 113 and a drive gear 114 of the gear mechanism via a hole through the center of the roller clutch 113 and drive gear 114. The rod shaft 118 includes a threaded gear 118b and an indentation 118c (shown in FIGS. 1E and 1F), in which the threaded gear 118b is capable of coupling to the drive gear 114 between internal threads of the drive gear 114 when the gear mechanism is in an engaged position. For example, when the gear mechanism is in the engaged position, the push spine component 110 can move in response to a movement (e.g., a linear advancement) by the injection shaft component 102. The drive gear 114 can be structured to include external threads that couple to the injection shaft component 102 between the threads of the threaded cylindrical section 102b. The drive gear 114 can be structured to include internal threads located within the hole through its center (shown in FIG. 1F), such that the drive gear 114 rotates in response to a movement of the shaft component 102. The gear mechanism can include a gear 115 connected to the rod shaft 118 and located at a fixed position on the rod shaft 118 between the threaded gear 118b and the indentation 118c. In some exemplary configurations, the gear 115 can be configured as part of the rod shaft 118. The gear 115 can be structured to include outer threads that couple between the threads 110b of the link structures 110a of the spine component 110 so that the rotation of the drive gear 115 (e.g., resulting from a rotation of the drive gear 114 when in the gear mechanism is in the engaged position) can be translated into the movement of the link structures 110a of the spine component 110 which, in turn, pushes the piston or plunger in the cartridge 120 to press a determined amount of the medicine in the cartridge 120 out of the cartridge 120 and device, e.g., through the detachable needle structure 125 and into the patient's body (e.g., via the protruding needle 124 that can penetrate into the patient's body to dispense the medicine). The gear mechanism can include a spring 117 surrounding the rod shaft 118 and located under the gear 115, in which the spring 117 provides a compressive force when compressed. The roller clutch 113 is configured to prevent the drive gear 115 from rotating in more than one direction.

Figure 1F:
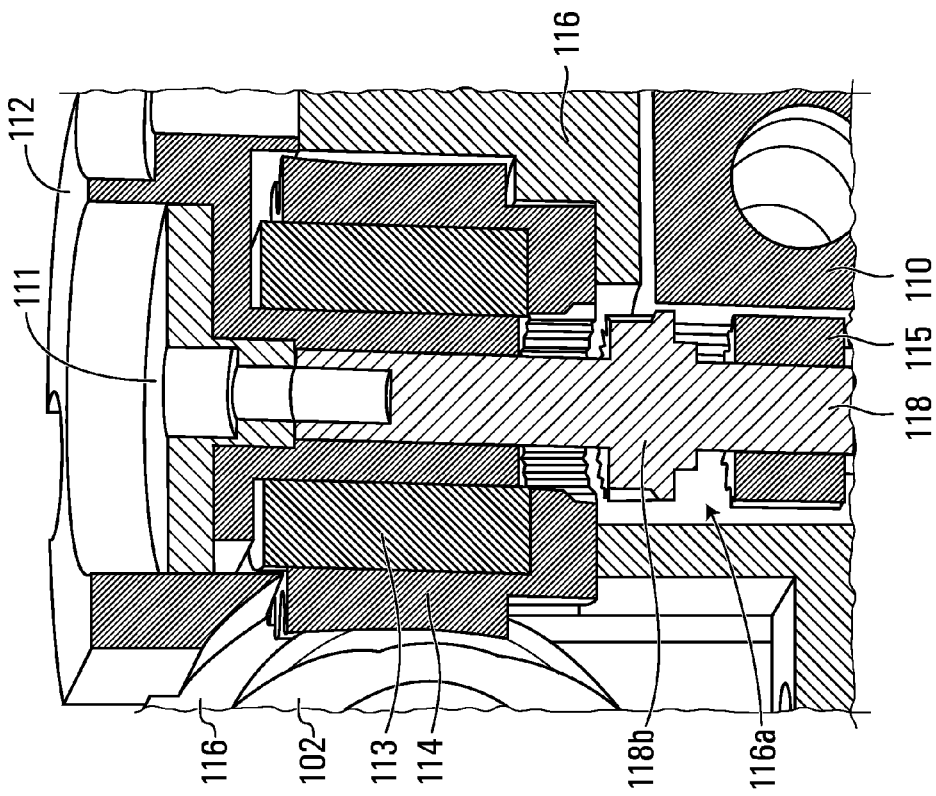
Figure 1E:
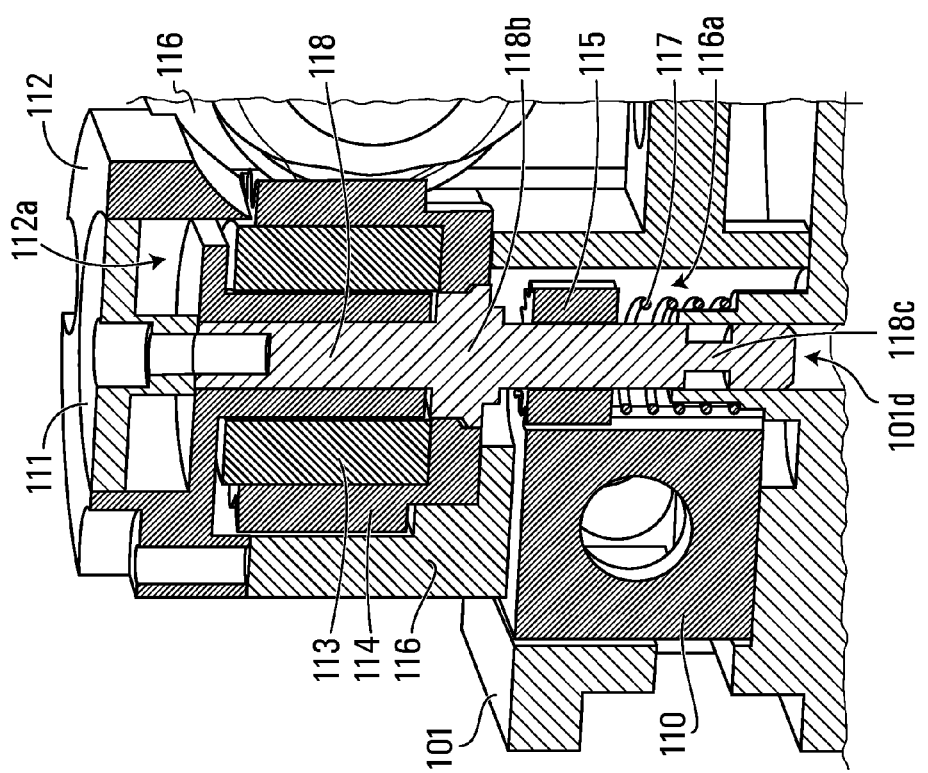

FIG. 1E shows a schematic of the gear mechanism in the engaged position, and FIG. 1F shows a schematic of the gear mechanism in the disengaged position. For example, the advancement of the button 111 advances the rod shaft 118 from the engaged position to the disengaged position that disengages the drive gear 114 from the threaded gear 118b of the rod shaft 118, e.g., allowing the push spine component 110 to move independent of the injection shaft component 102. In this example, the button casing structure 112 can include a recessed cavity 112a that permits the button 111 to travel (e.g., linearly advance into the recessed cavity 112a) when the button 111 is pressed. For example, the advancement of the button 111 advances the rod shaft 118 through a channel formed by the holes through the center of the button casing 112 and the drive gear 114, an actuator chamber 116a of the mechanism encasement structure 116, and a housing chamber 101d of the housing structure 101. The advancement of the rod shaft 118 displaces the threaded gear 118b of the rod shaft 118 from its engaged alignment with the internal threads of the drive gear 114. The displacement of the threaded gear 118b of the rod shaft 118 from the internal threads of the drive gear 114 uncouples the two components such that a movement of the injection shaft component 102 no longer affects the movement of the push spine component 110, and the injection shaft component 102 and the push spine component 110 are free to move independent of each other. For example, the gear mechanism can be maintained in the disengaged position using a clasp component 109 that is encased within the housing structure 101 and structured to include a notch 109a capable of coupling to the indentation 118c of the rod shaft 118 to lock the rod shaft 118 in the disengaged position, as shown later in FIG. 4B.

Figure 2A:
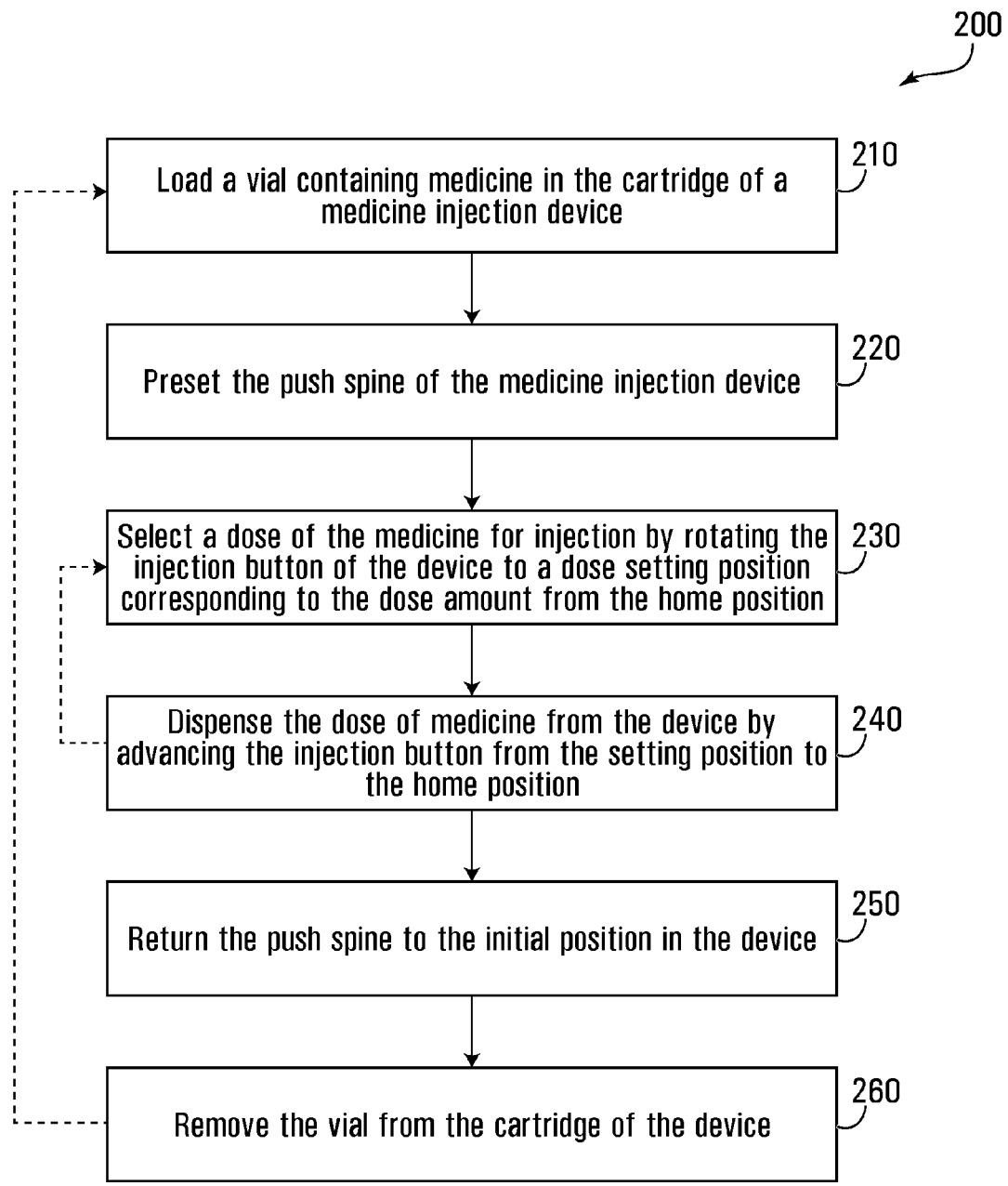
FIGS. 2A and 2B show block diagrams of processes to operate the exemplary medicine injection device.

FIG. 2A shows a block diagram of an exemplary process 200 to operate a medicine injection device of the disclosed technology. The process 200 can include a process 210 to insert a cartridge containing a medicine into the cartridge holder of the medicine injection device. The process 200 can include a process 220 to preset the push spine of the medicine injection device, e.g., by moving the push spine component in a position to make contact with the abutting end of the cartridge in the cartridge holder. The process 200 can include a process 230 to select a dose amount of the medicine for injection, e.g., by rotating an injection component of the device to a dose setting position corresponding to the selected dose amount, e.g., in which the injection component is rotated from its initial or home position corresponding to a zero dose. The process 200 can include a process 240 to dispense the medicine in the amount of the selected dose from the device, e.g., by linearly advancing the injection component from the dose setting position to the home position of the injection component, which can rotate a drive gear coupled to the injection component to drive the movement of the spine component. The process 200 can optionally include repeating the processes 230 and 240, e.g., while the inserted cartridge contains medicine in an amount greater than a desired dose. The process 200 can include a process 250 to return the push spine component to its initial position in the device, e.g., such that the push spine component is not positioned within the cartridge holder. The process 200 can include a process 260 to remove the cartridge from the cartridge holder of the device. For example, after the implementation of the process 260, the process 200 can be repeated by implementing the process 210. In some examples, the process 200 can further include displaying on a display of the device at least one of the dose setting or the corresponding dose amount during and/or after the process 230. The process 200 can further include scanning an identification code on the exterior of the medicine cartridge with an optical scanner of the device.

Figure 2B:
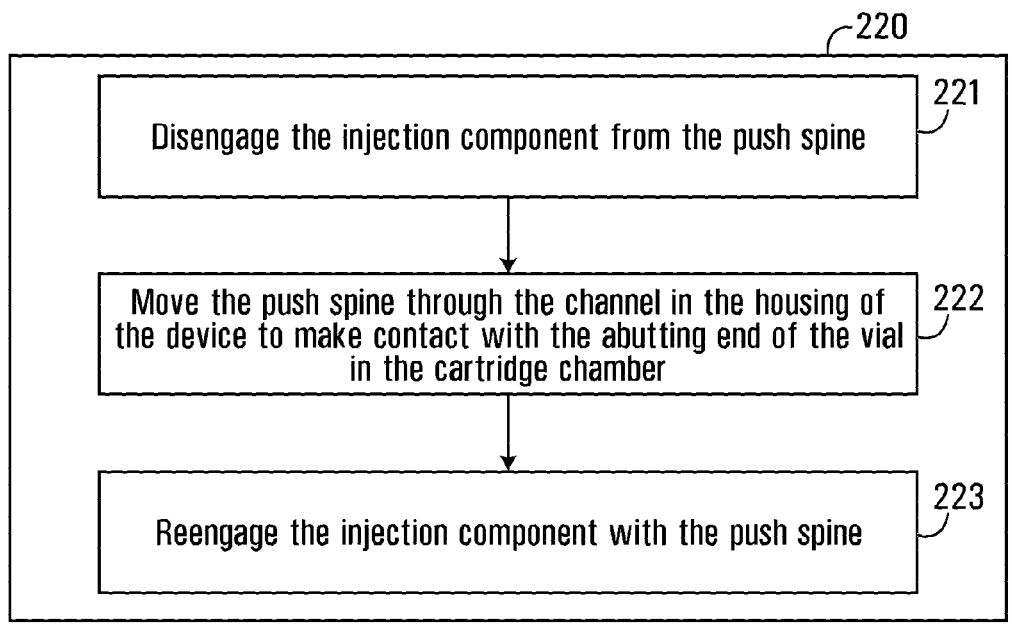

FIG. 2B shows a block diagram of the process 220 to preset the push spine of the medicine injection device. For example, the process 220 can include a process 221 to disengage the injection component from the push spine, e.g., by implementing a disengagement actuator (e.g., pressing the disengagement button on the exterior of the device) to advance the rod shaft from the engaged position to the disengaged position such that the threaded region of the rod shaft is not coupled to the internal threads of the drive gear, thereby allowing the spine component to move independent of the shaft component. For example, the process 220 can include a process 222 to move the push spine through the curved channel of the housing of the device to make contact with the abutting end of the cartridge in the chamber of the cartridge holder. For example, the process 220 can include a process 223 to reengage the injection component with the push spine, e.g., by implementing a reengagement actuator (e.g., pressing a release button on the slide button of the push spine component 110) to unlatch the notch of a clasping component from the indentation of the rod shaft 118 such that the gear mechanism returns to the engaged position.

Figure 3A:
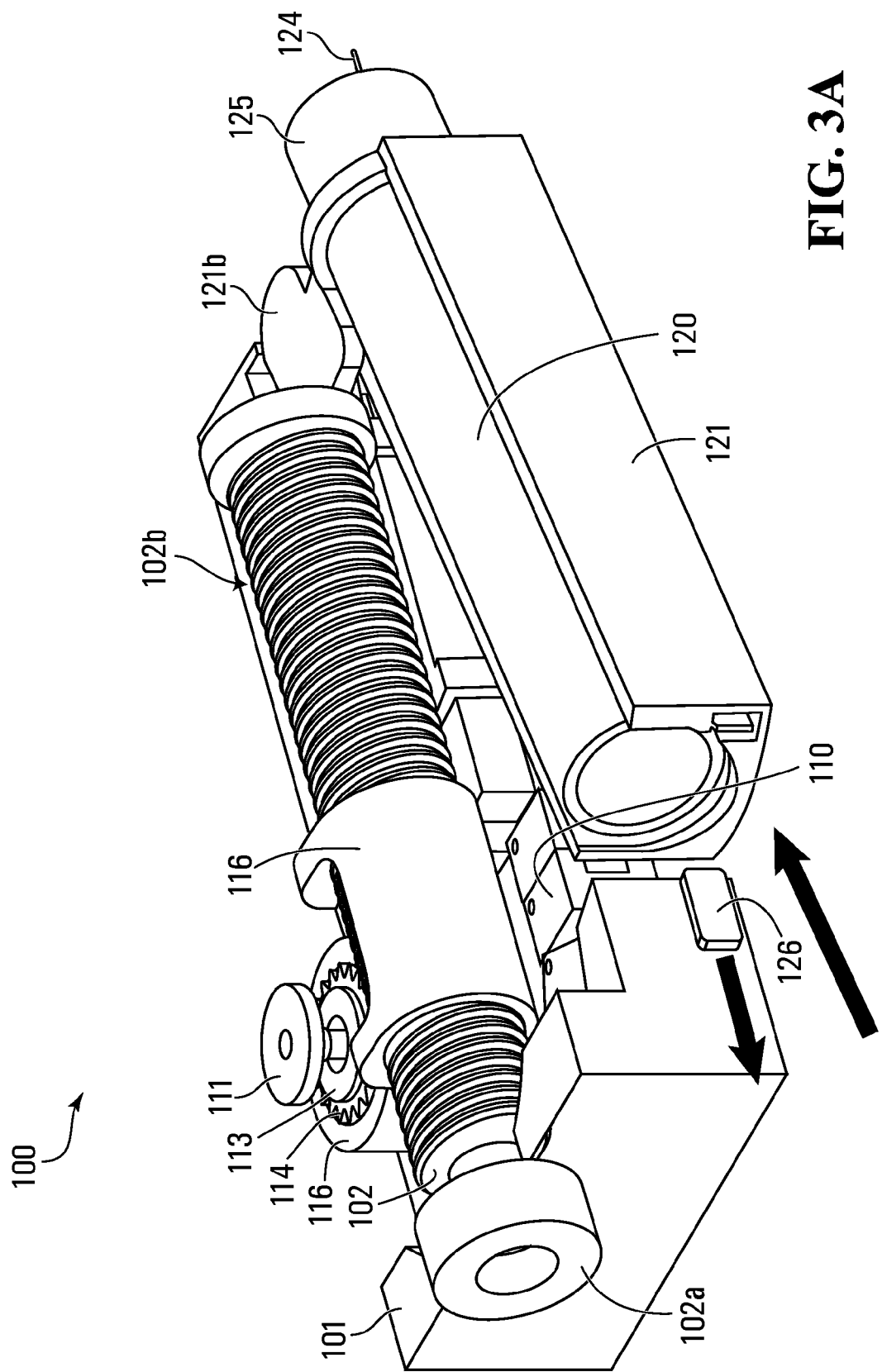
FIG. 3A shows a schematic illustrating a process to load a medicine cartridge into an exemplary medicine injection device.

FIGS. 3A-8 show schematics that illustrate the implementation of the exemplary process 200 using the exemplary medicine injection device 100. FIG. 3A shows a schematic illustrating the process 210 to load a cartridge containing medicine into the device 100. The process can include implementing the latch mechanism 126 to open the cartridge holder 121, e.g., by actuating the button of the latch mechanism 126 to unlock the cartridge holder 121 from the housing structure 101. The process can include inserting the cartridge 120 into the cartridge holder 121 while in the open position. The cartridge holder 121 can be configured to hold the cartridge 120 such that an opening at the end of the cartridge (for dispensing the contained medicine) is aligned with an opening at the distal end of the cartridge holder 121 having the detachable needle structure 125 with a protruding needle 124. The process can include returning the cartridge holder 121 to the closed position (e.g., which aligns the end of the cartridge 120 with the exit end of the curved channel 101a). For example, upon returning the cartridge holder 121 to the closed position, the latch mechanism 126 can be automatically engaged to lock the cartridge holder 121 in the position. The process can include attaching the needle structure 125 to the distal end of the cartridge holder 121.

Figure 3B:
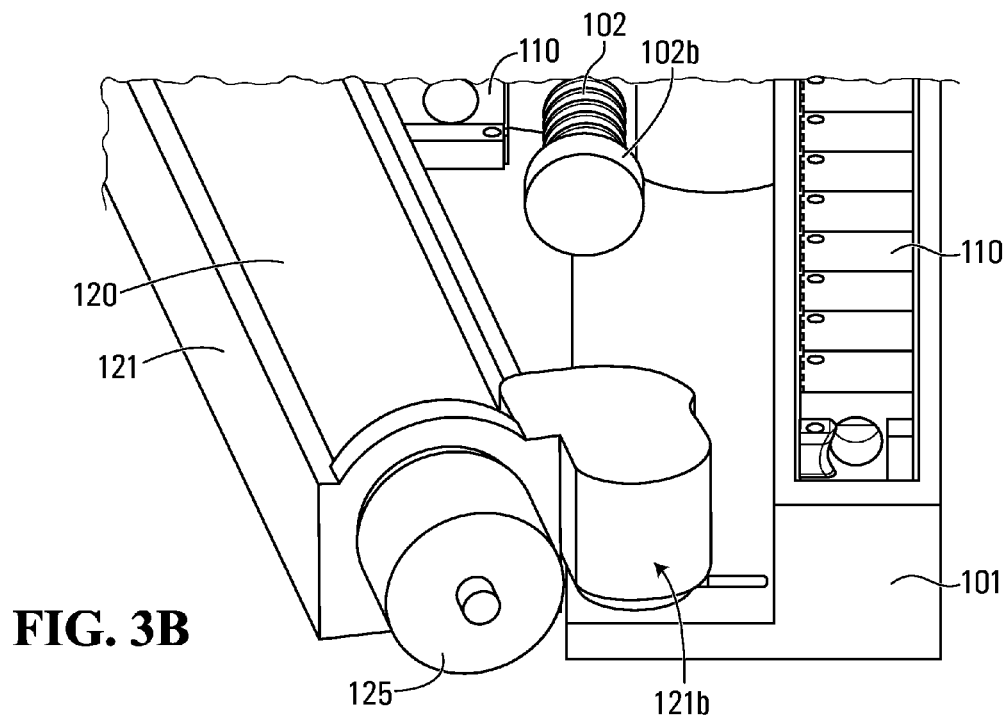
FIGS. 3B and 3C show schematics showing an exemplary torsion spring mechanism configured to enable loading/unloading of a medicine cartridge into the exemplary medicine injection device.
Figure 3C:
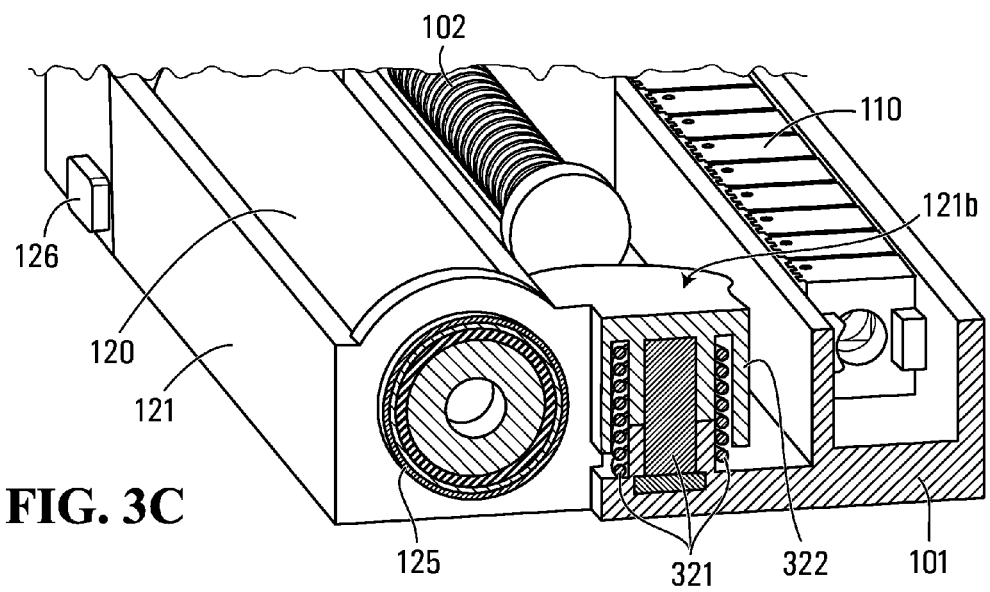

FIGS. 3B and 3C show schematics showing an exemplary torsion spring mechanism configured to couple the cartridge holder 121 to the housing structure 101 and enables the cartridge holder 121 to rotate to a load position upon unlocking of the latch mechanism 126 that allows for the loading/unloading of a medicine cartridge (e.g., the cartridge 120). As shown in FIG. 3B, the exemplary torsion spring mechanism of the rotational pivot joint structure 121b is implemented to rotate the cartridge holder 121 to the load position at a particular angle (e.g., which can be configured to 13 degrees from the closed position aligned with the terminal link of the push spine component 110, or to another angle based on design preference). FIG. 3C shows a cross section of the exemplary rotational pivot joint structure 121b that includes a torsion spring 321 which can be embedded in a spring housing component 322 of the cartridge holder 121 and the housing structure 101. The cartridge holder 121 is shown in the closed position in FIG. 3C, in which the torsion spring 221 of the rotational pivot joint structure 121b is compressed and the latch mechanism 126 locks the cartridge holder 121 in the closed position.

Figure 4A:
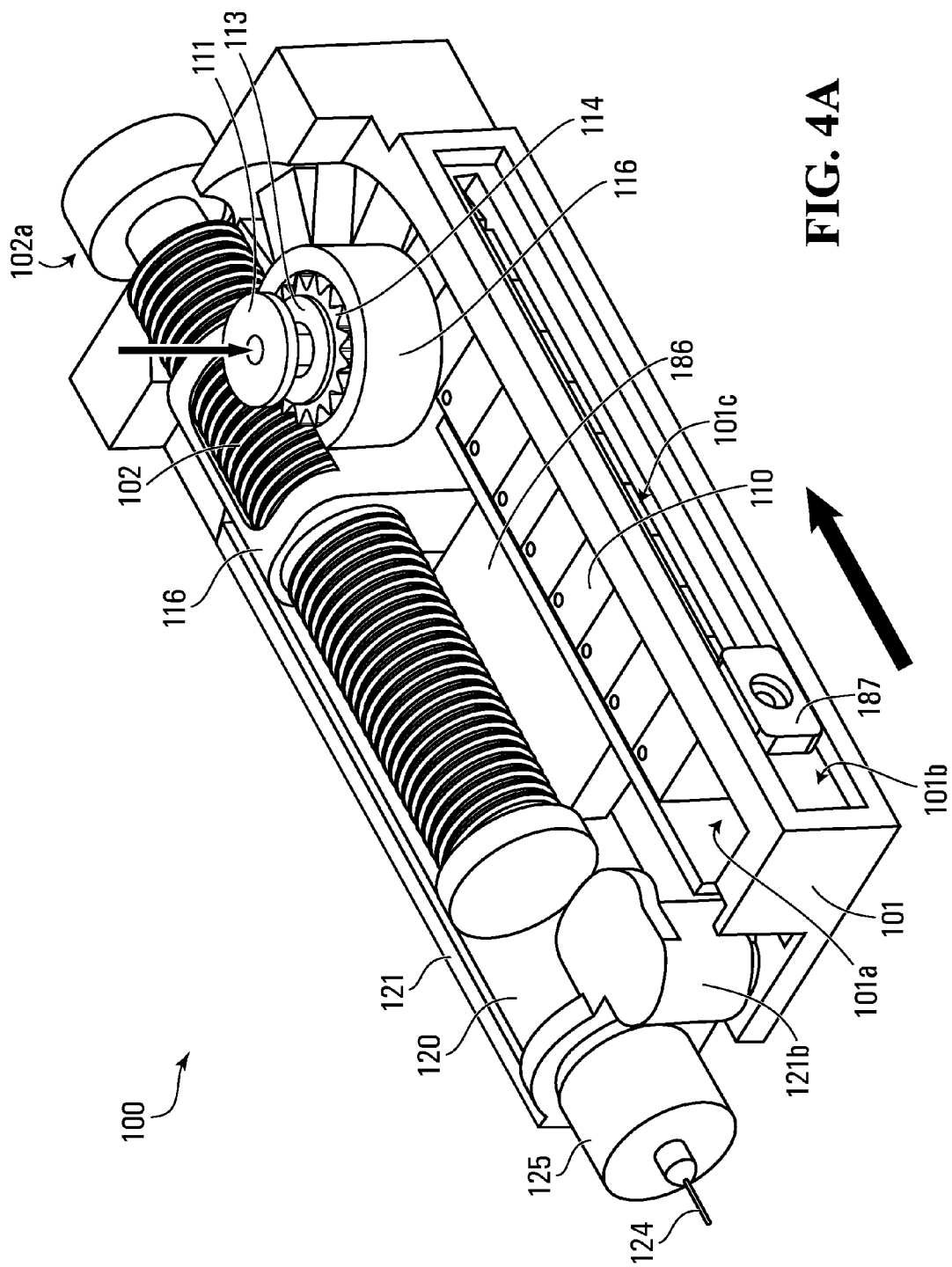
FIGS. 4A and 4B show schematics illustrating a process to prepare the exemplary medicine injection device for an injection.
Figure 4B:
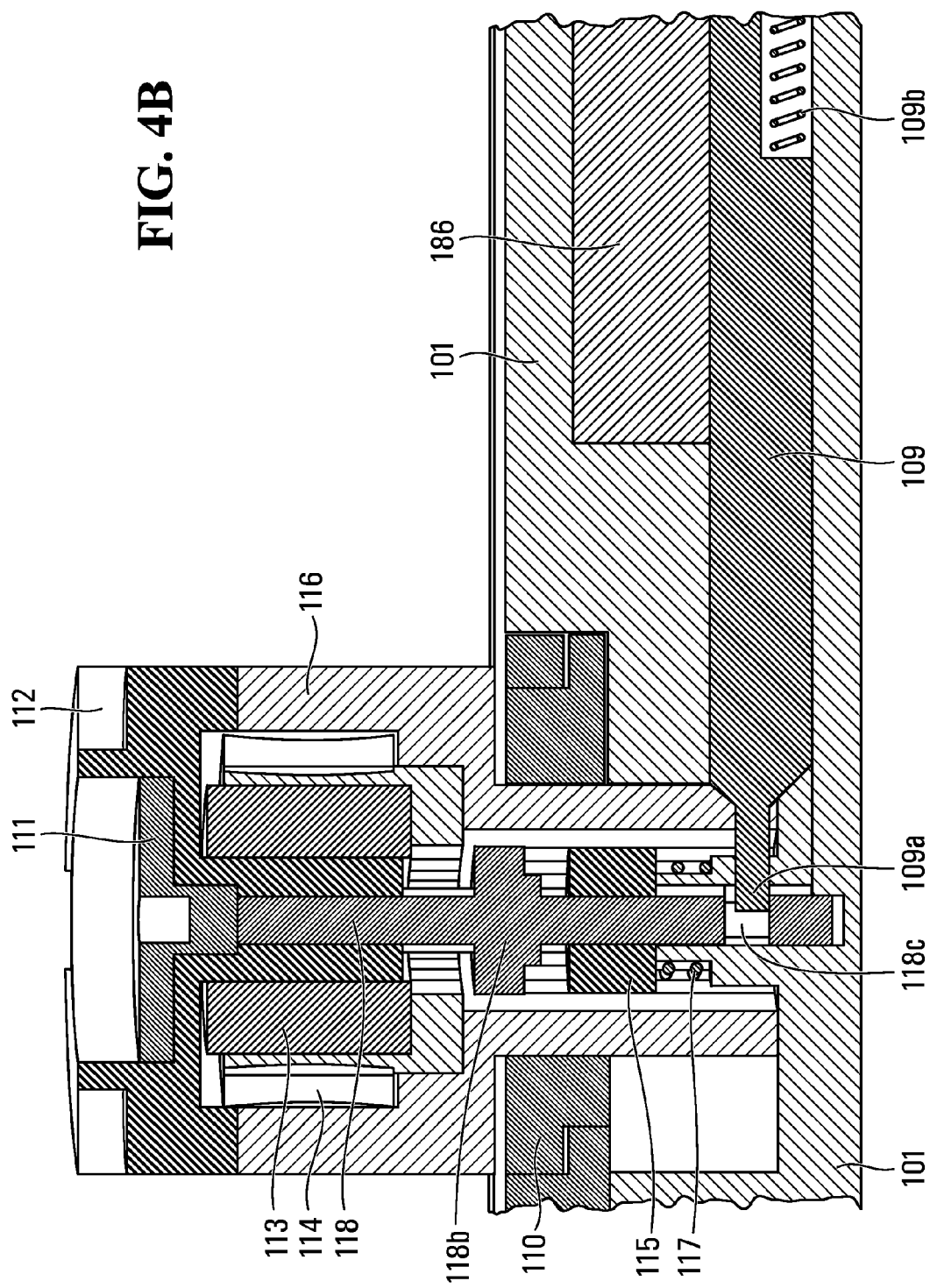

FIGS. 4A and 4B show a schematic illustrating the process 220 to preset the position the push spine component 110 of the device 100 to make contact with the cartridge 120 in the cartridge holder 121. FIG. 4A shows a schematic illustrating the process 221 to disengage the injection shaft component 102 from the push spine component 110 to allow the push spine component 110 to move independent of the injection shaft component 102. For example, the button 111 can be actuated to move the gear mechanism from the engaged position to the disengaged position, e.g., by pressing the button 111 into the recess of the button casing 112 to advance the rod shaft 118. For example, the advancement of the rod shaft 118 displaces the threaded gear 118b of the rod shaft 118 from its engaged alignment with the internal threads of the drive gear 114, such that a movement of the injection shaft component 102 no longer affects the movement of the push spine component 110.

The schematic in FIG. 4A also illustrates the process 222 to move the push spine component 110 through the curved channel 101a of the housing 101 to contact the abutting end of the cartridge 120 in the chamber of the cartridge holder 121. For example, while the gear mechanism is in the disengaged position, the push spine component 110 can be moved by sliding the button 187 along the recess 101b until the push spine component 110 abuts the cartridge 120.

FIG. 4B shows a schematic illustrating the process 223 to reengage the injection component with the push spine component, e.g., by implementing a reengagement actuator that releases the gear mechanism from the disengaged position. For example, the reengagement actuator can include the clasp component 109 that, when the gear mechanism is in the disengaged position, couples the notch 109a to the indentation 118c of the rod shaft 118 to lock the rod shaft 118 in the disengaged position and prevent its return to the engaged position. In one example, the clasp component 109 can be encased within an internal linear channel within the housing structure 101 that permits translational motion of the clasp component 109. In this example, the clasp component 109 can include a spring 109b that creates a force to drive the notch 109a into the housing chamber 101d to latch to the indentation 118c of the rod shaft 118 when the rod shaft 118 has been advanced far enough to align the indentation 118c with the notch 109a. In this example of the clasp component 109, a release structure can be configured to the clasp component 109 to pull the clasp component 109 back to an unlatched position, e.g., thereby releasing the rod shaft 118 to return gear mechanism to the engaged position. In another example of the clasp component 109, the clasp component 109 can be encased within an internal chamber within the housing structure 101 that permits rotational motion of the clasp component 109 about a pivot to rotate into the housing chamber 101d to latch to the indentation 118c of the rod shaft 118 when the rod shaft 118 has been advanced far enough to align the indentation 118c with the notch 109a. In this alternate example, the clasp component 109 can be coupled to a bar connected to a terminal link structure 110a of the push spine component 110 that protrudes out of the sliding button 187 when the push spine component 110 has been moved to abut the cartridge 120 in the cartridge holder 121. The bar can be actuated to retract the clasp component 109 in the opposite rotational motion such that the clasp component 109 releases the rod shaft 118 to return the gear mechanism to the engaged position. For example, the bar can be actuated by pressing the bar into the sliding button 187.

Figure 5:
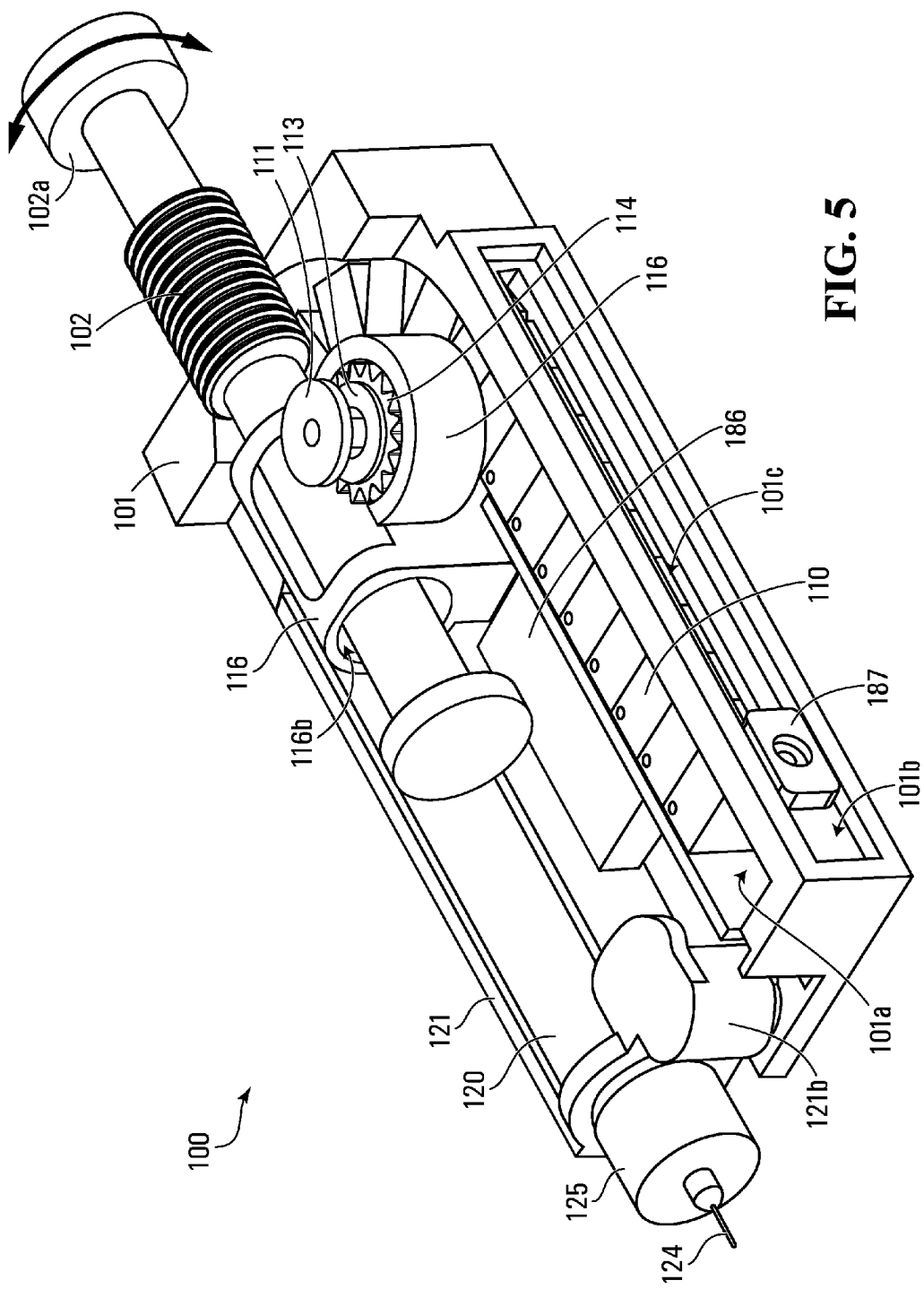
FIG. 5 shows a schematic illustrating a process to select a dose of medicine to dispense using the exemplary medicine injection device.

FIG. 5 shows a schematic illustrating the process 230 to select a dose of medicine to dispense using the exemplary medicine injection device 100. The process can include rotating the injection shaft component 102 to a dose setting position from the home position to the select a dose amount corresponding to the dose setting position. In the disclosed embodiment of the medicine injection device 100, the dose setting and injection mechanism is configured to set a dose by rotating the injection shaft component 102 and to inject the selected dose by translationally advancing the injection shaft component 102. For example, the dose setting functionality of dose setting and injection mechanism can be configured such that rotation of the injection shaft component 102 does not actuate a motion of the gear mechanism. The injection shaft component 102 can be configured to rotate in both directions, e.g., such that the dose amount can be reduced prior to injection, for example, in an instance where the dose was set to high and the desired dose is a lesser amount. In some examples, the injection shaft component 102 can be rotated such that a clicking sound is produced to correspond to a dose setting (e.g., such as clicking for each 100 μL set by the rotation).

Figure 6A:
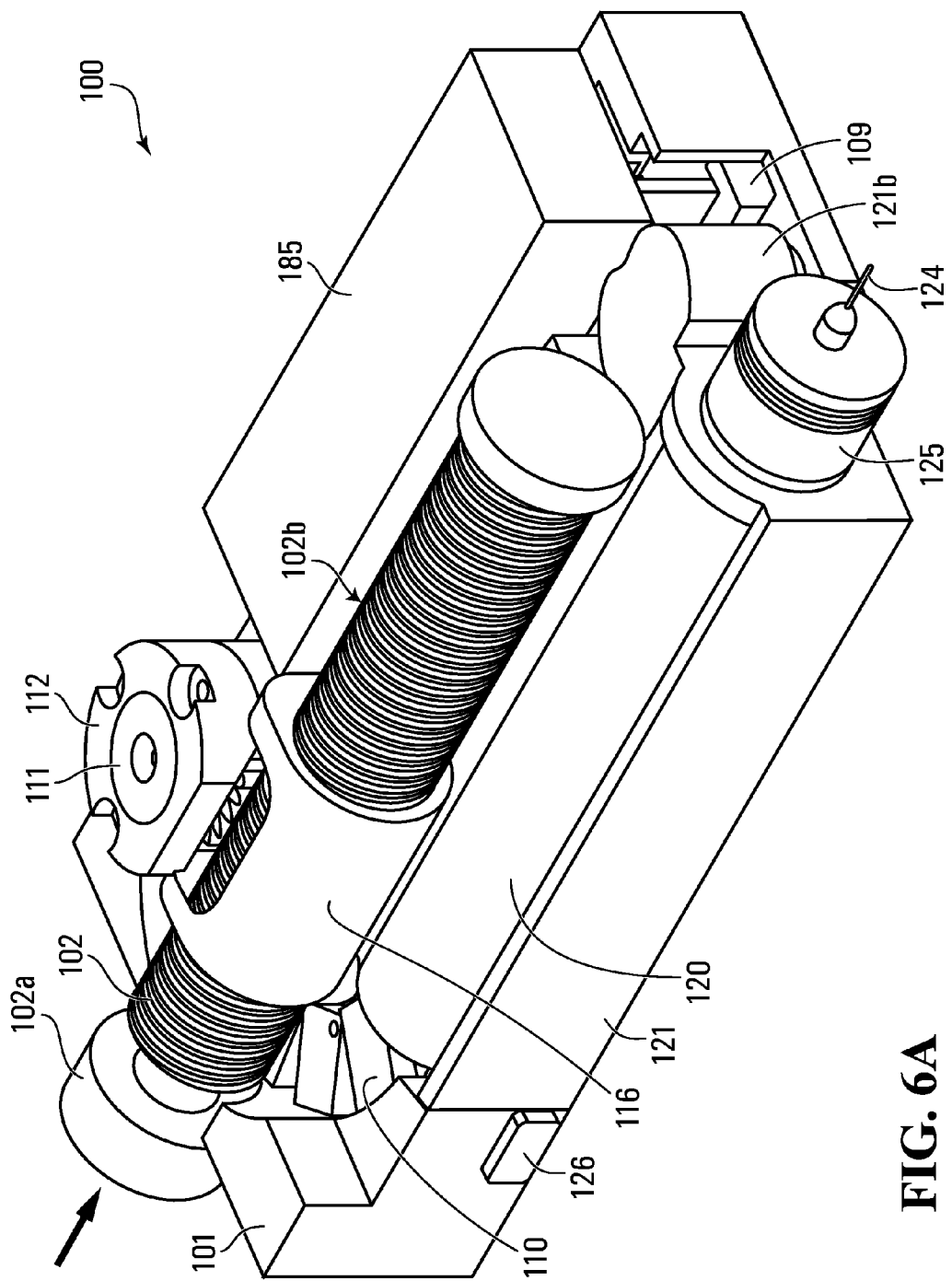
FIGS. 6A and 6B show schematics illustrating a process to dispense the dose of medicine using the exemplary medicine injection device.
Figure 6B:
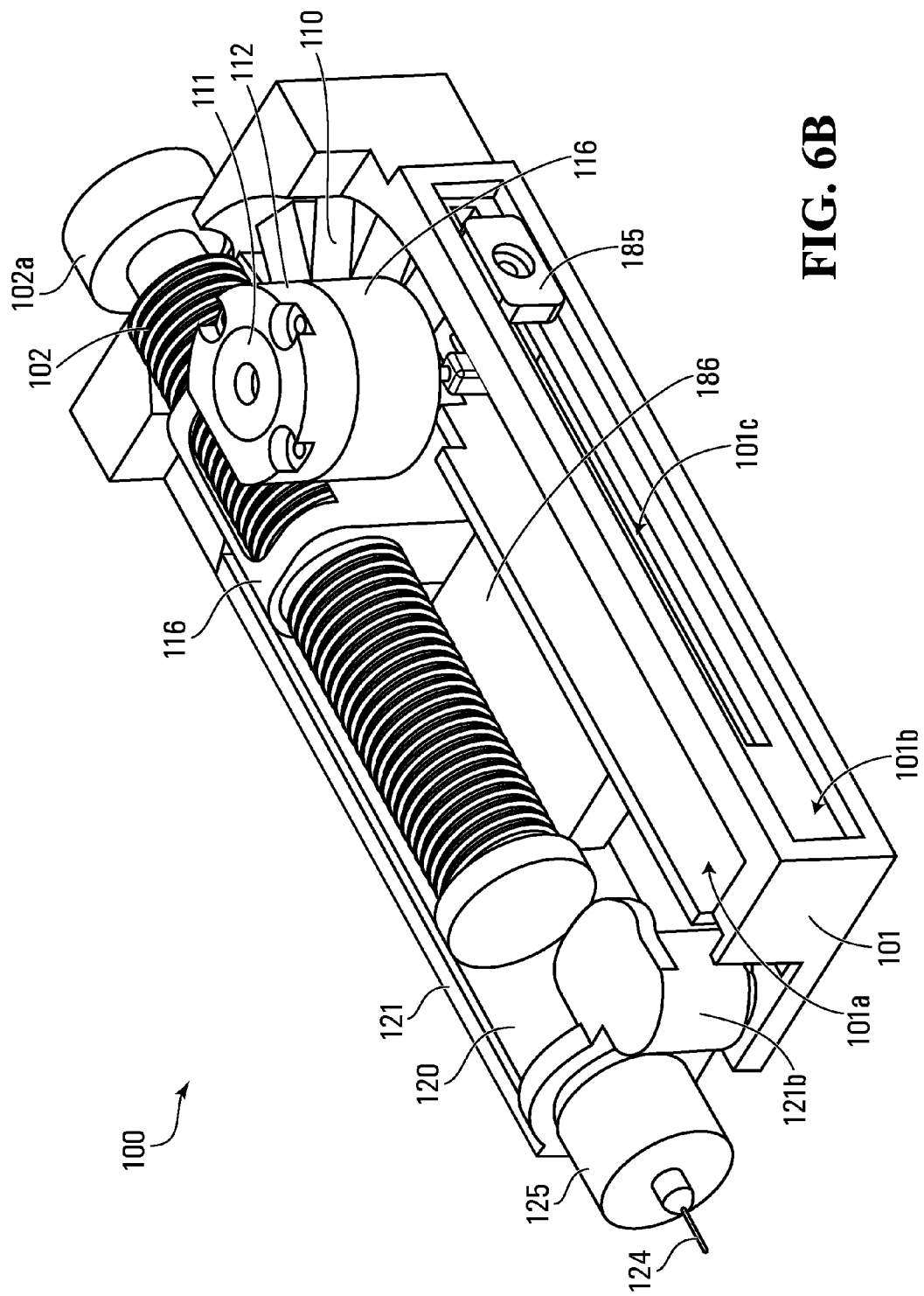

FIGS. 6A and 6B show schematics illustrating the process 240 to dispense the dose of medicine using the exemplary medicine injection device 100. The cartridge 120, which can be loaded into and removed from the chamber of the cartridge holder 121, includes a first end structured to interface with a cap of the detachable needle structure 125 to deliver the medicine to the injection needle 124 and a second end (e.g., an abutment end) with a movable plunger which interfaces with the terminal end of the link structure of the spine component 110. In operation, the spine component 110 is moved to cause a responding movement of the plunger in the cartridge 120 to dispense the properly selected amount of the medicine from the device 100, e.g., into the patient's body. This process includes linearly advancing the injection shaft component 102 from the dose setting position to the home position such that the advancement of the injection shaft component 102 actuates the rotation of the drive gear 114 of the gear mechanism to actuate the rotation of the rod shaft 118, which in turn rotates the gear 115, and thus drives the movement of the push spine component 110 to push the abutment end of the cartridge 120 into the body of the cartridge to dispense the medicine from the detachable needle structure 125 via the injection needle 124. The roller clutch 113 of the gear mechanism can be configured to allow the drive gear 114 to rotate in only one direction (e.g., counterclockwise), e.g., which can prevent a pulling movement of the push spine component 110. For example, the advancement of the injection shaft component 102 actuates the push spine component 110 to push the abutment end to plunge the medicine in the cartridge 120 by a volume of corresponding to the selected dose. For example, after the implementation of the process 240, the push spine component 110 remains in contact with the abutment end of the cartridge 120 (e.g., within the chamber of the cartridge holder 121) for any subsequent medicine dose setting and dispensing implementations. FIG. 6B shows the push spine component 110 in the curved channel 101a in which the leading portion of the curved channel 101a is advanced within the chamber of the cartridge holder 121.

Figure 7A:
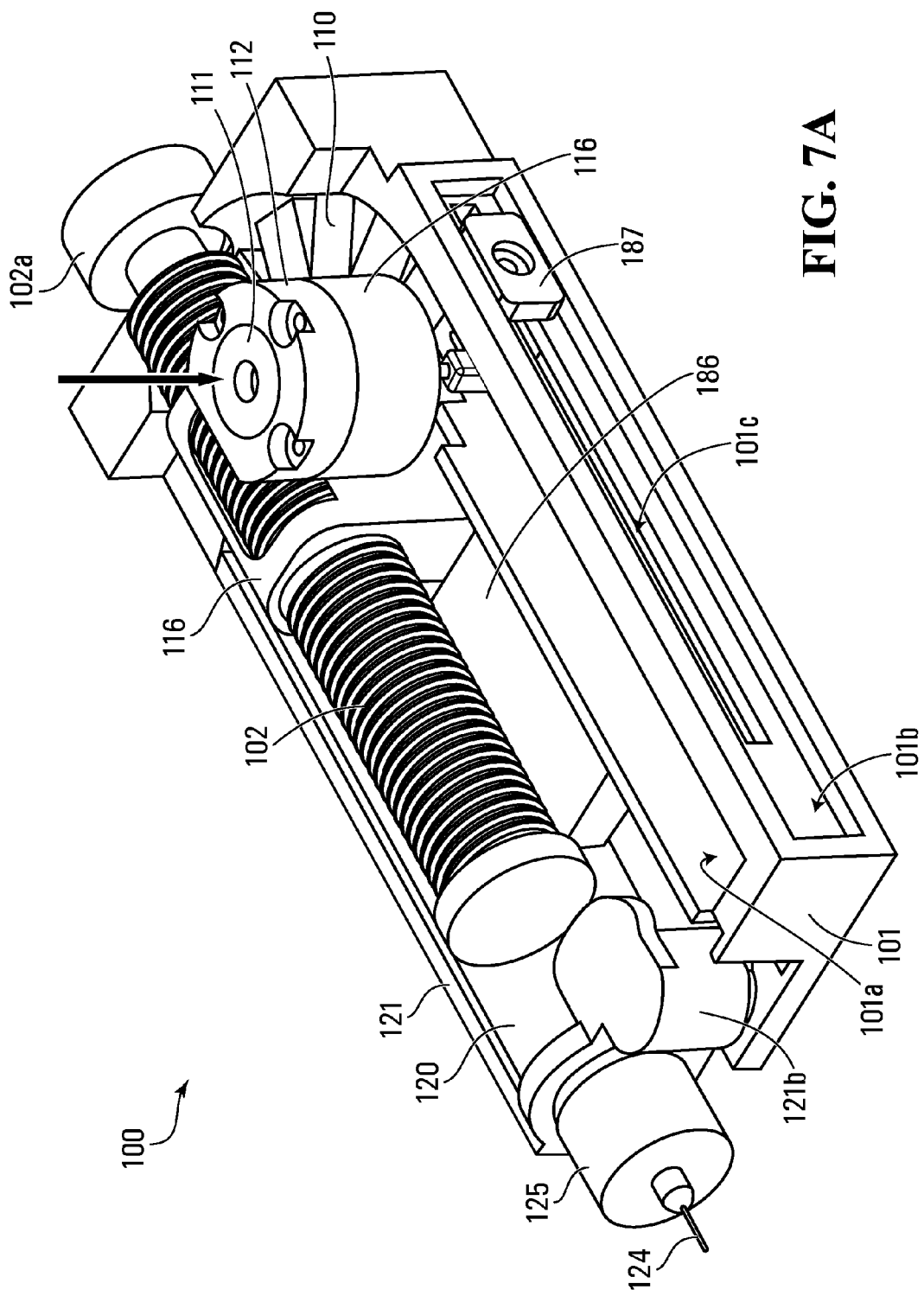
FIGS. 7A-7C show schematics illustrating a process to reset the exemplary medicine injection device.
Figure 7B:
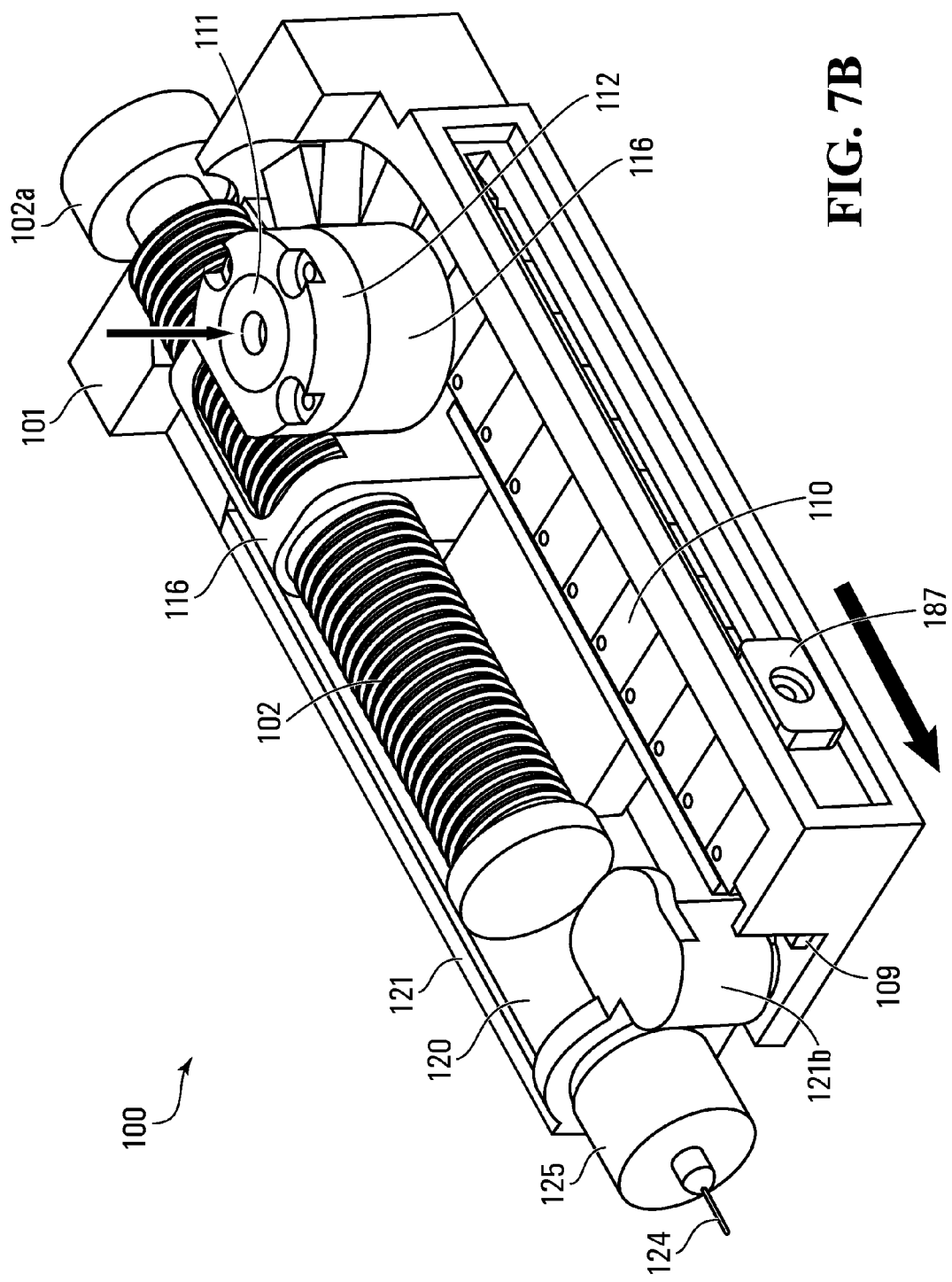
Figure 7C:
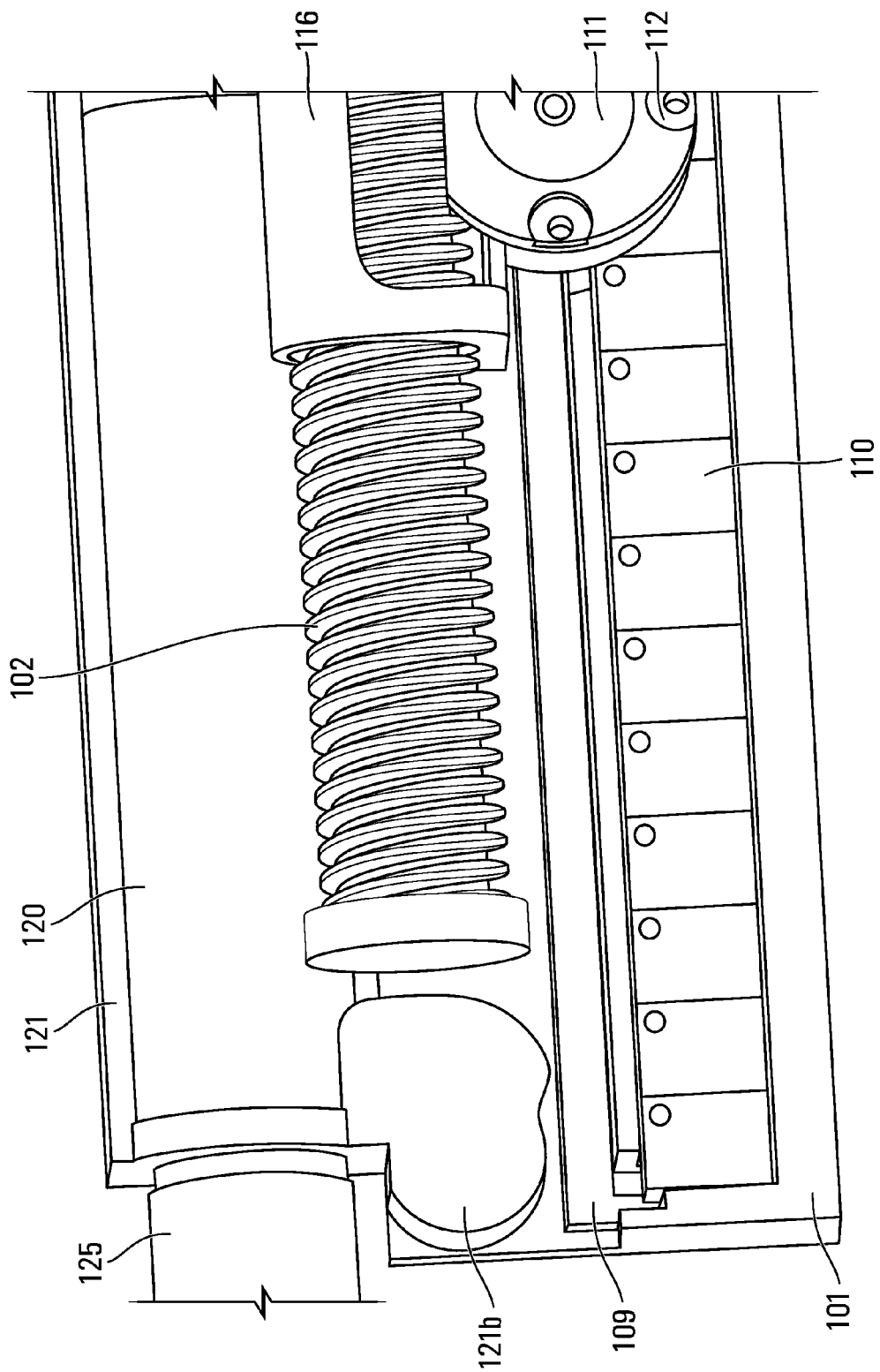

FIGS. 7A-7C show schematics illustrating a process 250 to reset the exemplary medicine injection device. The schematic of FIG. 7A illustrates the process 250 can include implementing the process 221 to disengage the injection shaft component 102 from the push spine component 110, e.g., by pressing the button 111 to advance the rod shaft 118 from the engaged position to the disengaged position. Subsequently, the push spine component 110 can be moved back to its initial position by pulling it through the curved channel 101a by sliding the sliding button 187 along the opening track 101c of the recess 101b, as illustrated in the schematics in FIGS. 7B and 7C.

Figure 8:
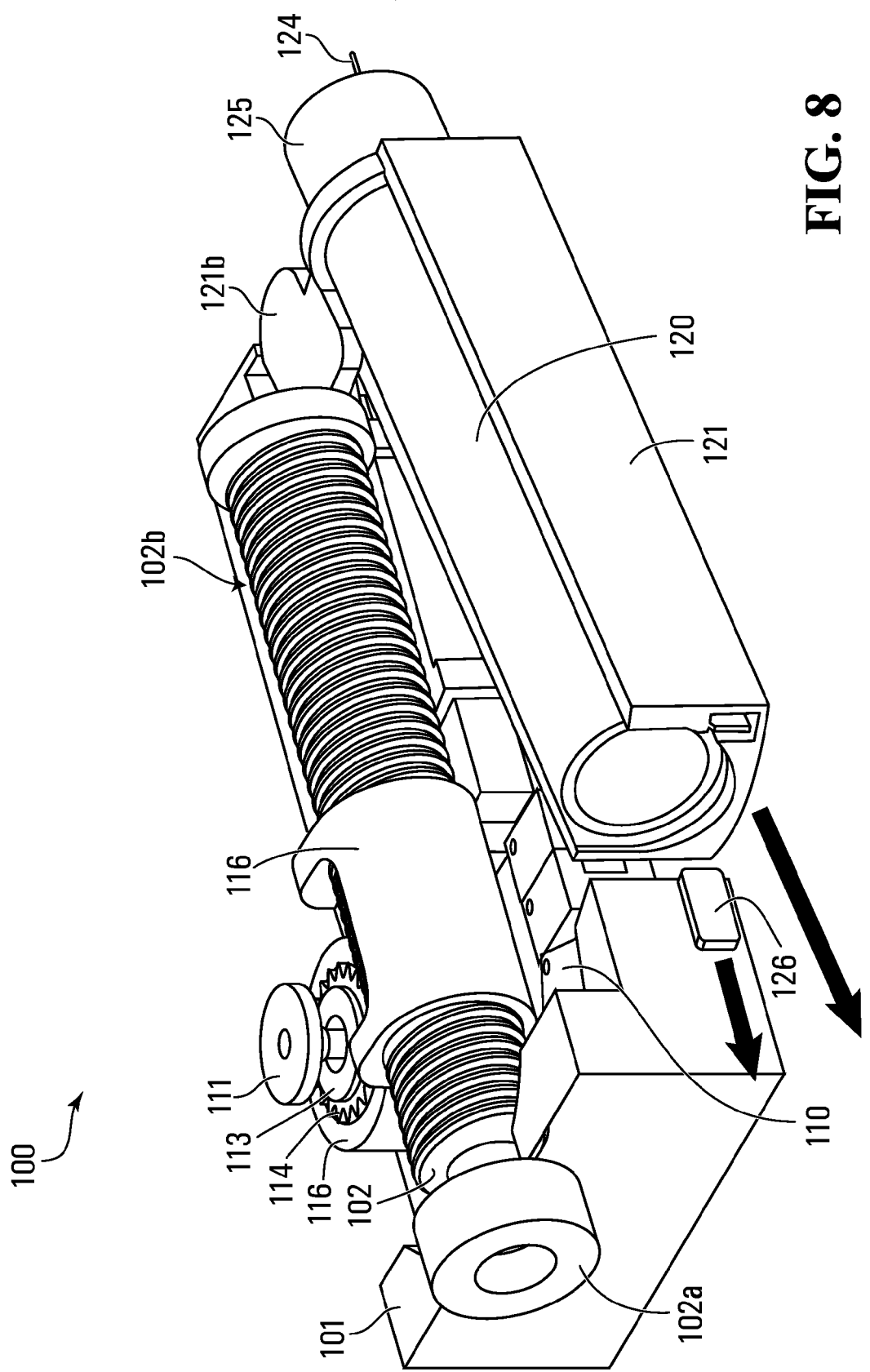
FIG. 8 shows a schematic illustrating a process to remove the used medicine cartridge from the exemplary medicine injection device.

FIG. 8 shows a schematic illustrating the process 260 to remove a used medicine cartridge from the exemplary device 100 and load a new medicine cartridge into the device 100. The process can include implementing the latch mechanism 126 to open the cartridge holder 121, e.g., unlocking the latch mechanism 126 such that the spring mechanism of the rotational pivot joint structure 121b rotates the cartridge holder 121 to the open position. The process can include removing the cartridge 120 from the cartridge holder 121 in the open position. The process can include inserting a new medicine cartridge into the cartridge holder 121 while in the open position. The process can include returning the cartridge holder 121 to the closed position (e.g., which aligns the end of the loaded new cartridge with the exit end of the curved channel 101a). For example, upon returning the cartridge holder 121 to the closed position, the latch mechanism 126 can be automatically engaged to lock the cartridge holder 121 in the position. In some examples, the process can include returning the cartridge holder 121 to the closed position and locking the cartridge holder 121 to the housing structure 101 without reloading a new medicine cartridge into the cartridge holder 121.

In another aspect of the disclosed technology, an integrated analyte monitoring and medicine treatment system is described for health management. In some exemplary embodiments, the system includes the disclosed medicine injection device and an analyte monitoring device (e.g., such as a glucose meter) that wirelessly communicate with a remote computerized system (e.g., server in the cloud), as well as with each other.

Figure 9:
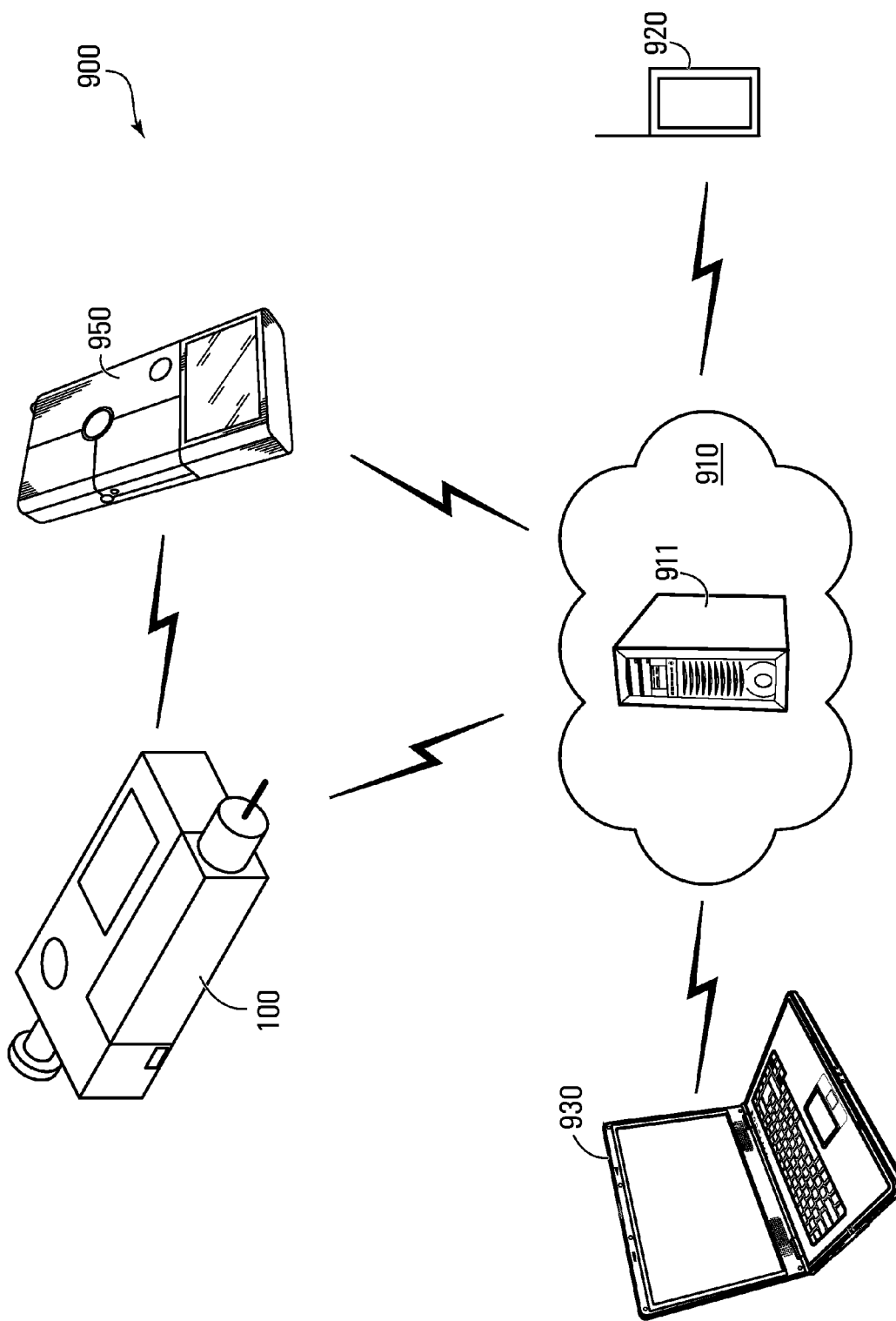
FIG. 9 shows a diagram of an exemplary system for health management including an exemplary medicine injection device, analyte monitoring device, and a cloud-based computing device.

FIG. 9 shows a diagram of an exemplary system 900 including an exemplary analyte monitoring device 950 and the medicine injection device 100 in communication with one or more cloud-based computing devices 910, e.g., such as a server 911. For example, the exemplary analyte monitoring device 950, the medicine injection device 100, and the cloud-based computer device 910 can be in communication through wired or wireless communications. Some examples for wireless communications include 3G wireless communication standards, 4G wireless communication standards including, LTE, WiFi, Bluetooth, and other suitable wireless communications via radio frequency waves and other electromagnetic waves. In some implementations, the cloud-based computing device 910 is in communication with other peripheral computing devices including a mobile device 920 (e.g., including, but not limited to a smart phone, tablet, laptop computer, etc.) and a computer device 930 (e.g., including, but not limited to a desktop, laptop, terminal or other computer, tablet or other computer medium).

The cloud-based computing device 910 can include a database to store and organize data received from devices of the system 900, e.g., such as the analyte monitoring device 950, the medicine injection device 100, or a user input terminal such as the computer 930 or mobile communication device 920, among others. For example, the information stored in the database of the cloud-based computing device 910 can be shared between any or all of the devices of the system 900. In some implementations, the database can exist on other the devices of the system 900 in addition or as an alternative to residing on the cloud-based computing device 910.

In some implementations, the system 900 includes the analyte monitoring device 950 and the medicine injection device 100 in communication with each other, in which the analyte monitoring device 950 communicates with the one or more cloud-based computing devices 910. In this example, the medicine injection device 100 communicates solely with the analyte monitoring device 950, which can relay the raw data or process the data and relay the processed data from the device 100 to the cloud-based computing device 910. For example, this exemplary configuration can permit the device 100 to operate with a scaled down communication system, e.g., which may reduce the number of components included in the device 100 and improve the overall power consumption rate of the device 100.

In some implementations, the system 900 includes multiple analyte monitoring devices 950 and/or multiple medicine injection device 100 in communication with the one or more cloud-based computing devices 910. For example, it may be desirable for a user to possess multiple medicine injection devices 100 that can be kept in various locations that a user may be frequently located, e.g., such as a user's home, car, workplace, gym, etc., while keeping a single analyte monitoring device 950 on the user's person. Additionally, the user may possess multiple analyte monitoring devices 950 in various desired locations. For example, since both the analyte monitoring devices 950 and medicine injection device 100 can include a user identification mechanism that permits only authorized users to operate the device, the user's data, settings, and other features personalized to the user remain secure on the devices.

The analyte monitoring device 950 can be configured as a blood analyte meter having a compact, all-in-one lancet/strip/meter structure that enables a user to perform a test using one hand. The analyte monitoring device 950 can be configured to be cassette based, e.g., enabling a user to easily change test strip and lancet cartridges. The analyte monitoring device 950 can be configured to include web-based tracking services and wireless communication devices and components. In some implementations, the analyte monitoring device 950 includes a plurality of analyte sensors (e.g., housed in an analyte sensor cartridge) and a plurality of lancets (e.g., housed in a lancet cartridge), in which a one-handed operation of an actuator mechanism can be implemented to ready the device for a test, prick the user to extract blood to be analyzed in the test, and reset the device for another use. For example, the actuator mechanism of the analyte monitoring device can be implemented to ready the device for a test by moving an analyte sensor (e.g., a test strip) forward to expose the sensor and advancing a firing component to a position for projection of a lancet. The actuator mechanism can subsequently be implemented to project (or fire) the lancet to prick a user to draw blood for analysis in the test. The actuator mechanism can be implemented to reset the device by ejecting the test strip and returning the components of the actuator mechanism to an initial position.

For example, in one exemplary embodiment, the analyte monitoring device 950 includes an analyte sensor module configured to hold a sensor cartridge structured to store analyte sensors, the analyte sensor module including an opening from which an analyte sensor advances to a testing position to expose at least a portion of the analyte sensor to outside of the analyte testing device. The analyte monitoring device 950 includes a lancet module configured to hold a lancet cartridge structured to store lancets. And, the analyte monitoring device 950 includes an actuator, in which the actuator includes: (i) a button; (ii) a first linking component coupled to the button and the analyte sensor module, in which the first linking component moves in response to a movement of the button including a movement between a first position and a second position or a movement between the second position and a third position; (iii) a second linking component coupled to the button and the lancet module, in which the second linking component moves in response to a movement of the button between the first position and the second position; (iv) a third linking component coupled to the second linking component and moveable in response to a movement of the second linking component; and (v) a lancet projecting component coupled to the third linking component. The analyte monitoring device 950 can be implemented such that a single operation of the button moves the analyte sensor to the testing position and moves the lancet projecting component from an initial position to a cocked position for projecting a lancet.

This exemplary embodiment of the analyte monitoring device 950 can be implemented in ways that provide one or more of the following features. For example, the analyte monitoring device 950 can include a processing unit coupled to a memory unit configured to store data, in which the processing unit is configured to evaluate data obtained from the analyte sensor module, lancet module, or information derived from data out of the analyte monitoring device 950. The processing unit can be configured to send a notification to a recipient based on the evaluated data. In some implementations, the processing unit can correlate individual instances of the data with time stamps, threshold values, alerts and user-entered information, e.g., including user-entered speech and text. The analyte monitoring device 950 can include a facility configured to transmit data obtained using a wireless protocol, or in other examples, a wired path, to other devices of the system 900. For example, the processing unit can be configured to keep track of inventory of lancets and analyte sensors, both within the device 950 and outside the device 950, e.g., such as test strip and lancet cartridges previously ordered and received by the user not in use within the device. For example, the processing unit can be configured to reorder inventory of lancets and analyte sensors. In some implementations, the processing unit can be configured to store voice recordings of diary information, e.g., for supplies used or ordered, food eaten, exercise, medication taken, and estimated calories burned. For example, the processing unit can be configured to produce a prompt to direct a user to use the device 950 according to at least one of a selected time or a selected time interval. The analyte sensor module of the analyte monitoring device 950 can include a temperature sensor to monitor temperature in the analyte sensor module. The analyte monitoring device 950 can also include an LCD touch screen display, e.g., to display a user interface for the user to interact with the device. Additionally, for example, the analyte monitoring device 950 can include a work light positioned to illuminate a lancet exit hole, as well as a work light positioned to illuminate an analyte sensor exit slot. In some implementations, the analyte monitoring device 950 can include a pedometer communicatively coupled with the processing unit configured to calculate, for example, the distance a user travels, speed of travel, and/or an amount of calories burned associated with the distance traveled. In some implementations, the analyte monitoring device 950 can be docked in a docking station that provides power and data connectivity to the device. In some implementations, the analyte monitoring device 950 can include a personal emergency response system (PERS) that includes a button for alerting a third party. For example, the PERS can be configured to perform the following functions, including, but not limited to, contact a third party, identify the device, provide health data associated with a user of the device, automatically contact a third party in response to health data associated with a user of the device, notify a third party as an urgency level of an emergency, and determine identity of a third party to be contacted.

The system 900 includes a data management and interface application that can be operated to manage the data stored in the database and associated with the medicine dispensing device 100 and the analyte monitoring device 950, as well as other forms of data inputted into the system 900 (e.g., by the user). The application can be operated on any of the devices of the system 900 with the same or varying amount of controls or functionalities, for example, based on a user interface presented to the devices, e.g., such as the analyte monitoring device 950, the cloud-based computing devices 910, the mobile device 920, the computer 930, and the medicine injection device 100. In some examples, the exemplary mobile device 920 operates a mobile application including a mobile user interface that is adapted for the particular mobile device.

The user interface of the data management and interface application in the system 900 is configured to provide a functional interface for a user to manage health information. For example, the application provides a health information and management interface that includes several interactive features that display information, e.g., including analyzed health information, and allow a user to input data. For example, the exemplary user health information and management interface can include a presentation of the data from the analyte monitor device 950 (e.g., raw data, analyzed data, and/or summary data), data from the medicine injection device 100 (e.g., raw data, analyzed data, and/or summary data), and data received as input from a user of the application interface.

In some exemplary embodiments, the application includes a user interface that can be accessed by each of a variety of users, e.g., including a patient (e.g., a diabetic person), a caregiver (e.g., a nurse or doctor or family member), and a payer (e.g., an insurance company) to facilitate the sharing of information and to enhance the quality of care. For example, the UI of the application can be configured differently for each type of user. The application of the system 900 can be configured in a variety of modules, e.g., in which each module can include a distinct user interface or include an inclusive user interface for some or all of the modules. For example, in some implementations, the application includes a UI for analyte monitoring (e.g., glucose level monitoring), a UI for medicine dispensing (e.g., insulin dose injections), a UI for lifestyle tracking (e.g., diet, exercise, etc.), and a UI for user information. In one example, an analyte monitoring user interface can be presented on any of the devices of the system 900 to enable the user to identify individual patterns and changes in the level of analytical substances found in a bodily fluid (e.g., blood, saliva, or urine) of a patient, as well as guide (e.g., provide pertinent info/test data to support guidance) the user (e.g., patient, care taker, doctor, etc.) as to what actions to take based on the analyte level, e.g., such as the timing and dosage of a medication, meal planning, physical activities, or other interventions. For example, the application can include an inclusive UI with viewable information to the user providing the analyzed analyte level and/or dispensed medicine data, tags and details, user goal information, selectable sub categories (e.g., including, but not limited to, nutrition information such as carbohydrates, steps, exercise, and goal information), selectable data history information, personalized settings, and flagging/data storing/questions settings.

The exemplary health management application of the system 900 can be used to identify a pattern (or patterns) or a threshold (e.g., maximum or minimum) that are analyzed from the analyte monitoring data or obtained as input from the user. For example, such data patterns and thresholds can include an analyte testing regime pattern, a medicine injection regime pattern, a hypo- or hyper-blood analyte level pattern or threshold, a pattern of variability in analyzed or input data, and a comparative pattern to a particular standard. For example, the inclusion of such a variety of information can be displayed on a single display of any of the devices of the system 900, which greatly enhances the user's experience and provides functionalities that would not have been possible, or readily discernible, from data that is dispersed throughout multiple plots, or lists, etc. Based on an identified pattern or threshold, alerts or messages can be generated by the exemplary health management system 900 and displayed on a screen of any of the devices of the system 900, e.g., such as the analyte monitoring device 950, the cloud-based computing devices 910, the mobile device 920, the computer 930, and the medicine injection device 100. Other types of messages can also be generated for the user, e.g., including, but not limited to, reminders, encouraging messages, factoids, etc.

For example, actual analyte levels and fluctuations therein can be easily correlated to one or more of the factors presented to the user using the UI. For example, fluctuations in analyte levels can be correlated to a variety of factors, e.g., including, but not limited to, consumption of nutrients, injection of a particular medicine and other medications taken by the patient for other conditions outside the condition being monitored, a patient's exercise schedule, a patient's stress, sickness, and other factors that may be inputted health information and management interface. By providing such a detailed and comprehensive picture on a single display screen, e.g., with a properly selected granularity, the system 900 enables a user to determine the effects of a particular factor on the patient's analyte levels. Further, such correlations can be further analyzed to set alerts (or alarms or reminders) to predict, prevent and/or mitigate adverse effects of such factors before the analyte levels reach a critical limit. In some embodiments, a caregiver is alerted to a particular analyte level fluctuations through a text message, a phone call, an email or other communication methods.

The application of the system 900 provide the following exemplary features that are operated on and/or displayed on, for example, the analyte monitoring device 950 and/or the medicine injection device 100. The exemplary features include, but are not limited to: (1) event time stamping and updating to database (e.g., including time stamping data associated with an analyte level test, injection, status of devices, or user inputted data such as exercise, meals, moments of stress, illness, or other types of data); (2) event displaying to the user through the UI, in which the events are stored in a running log in the database; (3) displaying motivational messages and images before and/or after test results; (4) temperature checking of the analyte test module (e.g., to confirm safe exposure of the analyte test strips, as extreme high or low temperatures can damage stored strips); (5) comparative data checking with control results data; (6) consumables/disposables monitoring, e.g., of the test strips and lancets of the analyte monitoring device 950 and/or the medicine level in the medicine cartridge loaded in the cartridge holder of the medicine injection device 100; (7) providing tutorials (e.g., such as animations educating the user on testing/injecting procedure); (8) authenticating a user prior to any or certain operations of the device; and (9) providing emergency contact information (e.g., such as 911, emergency respondents, and user-identified contacts, such as family), as well as, in some implementations, alerting identified persons or entities in case of emergency. For example, the application can keep track of unused and used consumables/disposables by the device 950 and/or the device 100, keep track of ordered (and unused) consumables/disposables in the user's possession, as well as keep track of remaining stock (e.g., packages) by manufacturers that the application is in communication with (e.g., using the internet). For example, the application can contact the manufacturers of such consumables/disposables when the user's remaining stock is low and re-order the consumables/disposables, e.g., by communicating using links to e-commerce.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A device to dispense a medicine, comprising:
a housing configured to include a curved channel;
a cartridge holder coupled to the housing via a pivot joint, the cartridge holder including a chamber structured to encase a cartridge containing a medicine and the cartridge having a first opening that aligns with one end of the curved channel at an end of the chamber and a second opening at an opposite end of the chamber; and
a dose setting and injecting mechanism including:
(i) a spine component housed in the curved channel of the housing, the spine component including a plurality of link structures linked together to allow curved movement of the spine component within the curved channel, wherein the one end of the curved channel includes a channel opening interfaced with the first opening to enable the spine component to push against the cartridge for dispensing a selected amount of the medicine through the second opening,
(ii) a shaft component structured to include a threaded cylindrical section encased at least in part within the housing and a knob disposed at least in part outside of the housing,
(iii) a gear mechanism including a rod having a first gear and a second gear, the second gear coupled to the spine component, and a drive gear having a first gear engagement mechanism for engaging to the first gear and a second gear engagement mechanism for engaging to threads of the threaded cylindrical section of the shaft component, wherein, upon engagement of the first gear and the drive gear to each other, a linear movement of the shaft component moves the spine component, and (iv) a disengagement button coupled to the rod to disengage the first gear and the drive gear from each other, thereby allowing the spine component to move independent of the shaft component, wherein a rotation of the shaft component moves the shaft component to a distance from the housing that corresponds to the selected amount of the medicine.

2. The device of claim 1, wherein the pivot joint includes a torsion spring that causes the cartridge holder to rotate to an open position that exposes the first opening when the cartridge holder is unlocked from the housing.

3. The device of claim 2, further comprising a latching mechanism to lock the cartridge holder in a closed position in the housing and unlock the cartridge holder to allow the cartridge holder to rotate about the pivot joint to the open position.

4. The device of claim 1, further comprising a data processing unit, comprising:
a processor; and
a memory coupled to the processor,
wherein at least one of the selected amount of the medicine or a dispensed amount of the medicine is processed as data by the processor and stored in the memory.

5. The device of claim 4, further comprising an optical scanner coupled to the data processing unit and configured to scan an identification code located on an external surface of the cartridge when the cartridge is encased in the chamber, wherein the identification code corresponds to information about the medicine contained in the cartridge.

6. The device of claim 5, wherein the identification code includes a plurality of bars wrapped radially around the cartridge.

7. The device of claim 4, further comprising a wireless transmitter unit to transmit the data to a computing device.

8. The device of claim 4, further comprising a display unit to display the data.

9. The device of claim 4, further comprising sensors configured within a movement path of the shaft component to measure at least one of the rotation or the linear movement to indicate the selected dose, wherein the sensors are in communication with the data processing unit.

10. The device of claim 1, further comprising a detachable needle coupled to the exterior of the cartridge holder that aligns with the second opening to dispense the medicine from the device.

11. The device of claim 1, further comprising a clasp component encased within the housing and coupled to a bar connected to a terminal link structure of the spine component, wherein the clasp component locks the rod in a disengaged position when the disengagement button is actuated, and wherein the clasp component releases the rod to move to an engaged position when the bar is actuated based at least in part on movement of the spine component in the curved chamber toward the cartridge holder.

12. The device of claim 1, wherein the medicine includes insulin.

13. A health management system, comprising:
an analyte monitoring device to determine a concentration level of an analyte;
a computing system in communication with the analyte monitoring device, the computing system comprising:
(a) a memory unit, and
(b) a processor configured to process data; and
a medicine injection device in communication with at least one of the analyte monitoring device or the computing system, the medicine injection device comprising:
(a) a housing configured to include a curved channel,
(b) a cartridge holder coupled to the housing via a pivot joint, the cartridge holder including a chamber structured to encase a cartridge containing a medicine and the cartridge having a first opening that —aligns with a first end of the curved channel when encased in the chamber and a second opening, and
(c) a dose setting and injecting mechanism including:
(i) a spine component housed in the curved channel of the housing, the spine component including a plurality of link structures linked together to allow curved movement of the spine component within the curved channel, wherein the first end of the curved channel includes a channel opening interfaced with the first opening to enable the spine component to push against the cartridge for dispensing a selected amount of the medicine through the second opening,
(ii) a shaft component structured to include a threaded cylindrical section encased at least in part within the housing and a knob disposed at least in part outside of the housing,
(iii) a gear mechanism including a rod having a first gear and a second gear, the second gear coupled to the spine component, and a drive gear having a first gear engagement mechanism for engaging to the first gear and a second gear engagement mechanism for engaging to threads of the threaded cylindrical section of the shaft component, wherein, upon engagement of the first gear and the drive gear to each other, a linear movement of the shaft component moves the spine component, and
(iv) a disengagement button coupled to the rod to disengage the first gear and the drive gear from each other, thereby allowing the spine component to move independent of the shaft component,
wherein a rotation of the shaft component moves the shaft component to a distance from the housing that corresponds to the selected amount of the medicine.

14. The system of claim 13, wherein the computing system is further configured to transmit and/or receive at least one of: (a) data obtained from the analyte monitoring device, (b) data obtained from the medicine injection device, or (c) information derived from data from a user-operated computing device, based on a wireless or wired communication protocol.

15. The system of claim 14, wherein the processor is configured to send a notification to a recipient based on the wireless or wired communication protocol.

16. The system of claim 13, wherein the processor is configured to keep track of inventory of lancets and analyte sensors of the analyte monitoring device.

17. The system of claim 16, wherein the processor is configured to reorder the inventory of one or both of the lancets and the analyte sensors.

18. The system of claim 13, wherein the processor is configured to produce a prompt to direct a user to use one or both of the analyte monitoring device and the medicine injection device at a predetermined time or time interval.

19. The system of claim 13, wherein the computing system is configured to process and store user input data selected from the group consisting of: supplies used, supplies ordered, food eaten, duration, type and/or intensity of an exercise, type, dosage and/or time of medication taken, and estimated calories burned.

* * * * *